United States Patent [19]
Ditzel et al.

[11] Patent Number: 5,939,585
[45] Date of Patent: *Aug. 17, 1999

[54] PROCESS FOR THE CARBONYLATION OF AN ALCOHOL

[75] Inventors: Evert Jan Ditzel; Michael David Jones, both of North Humberside; Andrew David Poole, Hampshire, all of United Kingdom

[73] Assignee: BP Chemicals Limited, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/954,423

[22] Filed: Oct. 20, 1997

Related U.S. Application Data

[63] Continuation of application No. 08/458,442, Jun. 2, 1995, abandoned.

[30] Foreign Application Priority Data

Feb. 21, 1995 [GB] United Kingdom .................. 9503382

[51] Int. Cl.$^6$ ............................ C07C 51/12; C07C 67/36
[52] U.S. Cl. ........................... 562/519; 560/232; 562/891
[58] Field of Search ............................ 560/232; 562/519, 562/891

[56] References Cited

U.S. PATENT DOCUMENTS

| | | |
|---|---|---|
| 3,769,329 | 10/1973 | Paulik et al. . |
| 4,046,807 | 9/1977 | Kuckertz . |
| 4,101,450 | 7/1978 | Hwang et al. . |
| 4,136,104 | 1/1979 | Hwang et al. . |
| 4,500,474 | 2/1985 | Lyons et al. . |
| 4,514,336 | 4/1985 | Ryan et al. . |
| 4,640,802 | 2/1987 | Drent . |
| 4,658,053 | 4/1987 | Green . |
| 4,664,851 | 5/1987 | Drent . |
| 4,681,707 | 7/1987 | Alper et al. . |
| 5,268,505 | 12/1993 | Delis et al. . |

FOREIGN PATENT DOCUMENTS

| | | |
|---|---|---|
| 0031606 | 7/1981 | European Pat. Off. . |
| 0072055 | 2/1983 | European Pat. Off. . |
| 0075335 | 3/1983 | European Pat. Off. . |
| 0075337 | 3/1983 | European Pat. Off. . |
| 0083121 | 7/1983 | European Pat. Off. . |
| 0085204 | 8/1983 | European Pat. Off. . |
| 0087870 | 9/1983 | European Pat. Off. . |
| 0120631 | 10/1984 | European Pat. Off. . |
| 0636599 | 2/1995 | European Pat. Off. . |
| 0643034 | 3/1995 | European Pat. Off. . |
| 1234641 | 6/1971 | United Kingdom . |
| 1468940 | 3/1977 | United Kingdom . |
| 1523346 | 8/1978 | United Kingdom . |
| 1538783 | 1/1979 | United Kingdom . |
| 2029409 | 3/1980 | United Kingdom . |

OTHER PUBLICATIONS

Pursiainen et al., "Synergistic . . . Ruthenuim–Rhodium . . . Homologation", J. Organometallic Chem., vol. 314, pp. 228–230, 1986.
Journal of Molecular Catalysis, 39 (1987) 115–136, B.L. Smith, G.P. Torrance, M.A. Murphy and A. Aguilo.
Mechanistic Aspects of Transition–Metal–Catalyzed Alcohol Carbonylations, Thomas W. Dekleva and Denis Forster. Inorganica Chimica Acta. 221 (1994) 109–116.
Journal of Organometallic Chemistry, 314 (1986) 227–230 J. Pursiainen et al.
Journal of Organometallic Chemistry, 462, (1993) 347–352, B.T. Heaton, C. Jacob and S. Moffett.
Journal of Molecular Catalysis, 40 (1987) 71–82, Gerard Jenner and Gustave Bitsi.
C&EN, Feb. 27, 1984, pp. 21–22, J. Haggin.

Primary Examiner—Samuel Barts
Assistant Examiner—Rosalynd Keys
Attorney, Agent, or Firm—Morgan & Finnegan, LLP

[57] ABSTRACT

A process for the carbonylation of a $C_1$ to $C_4$ alkyl alcohol and/or a reactive derivative thereof by contacting a $C_1$ to $C_4$ alkyl alcohol and/or a reactive derivative thereof with carbon monoxide in a liquid reaction composition in a carbonylation reactor in the presence of (a) a rhodium catalyst (b) an alkyl halide, and (c) as promoter, at least one of ruthenium and osmium.

10 Claims, 6 Drawing Sheets

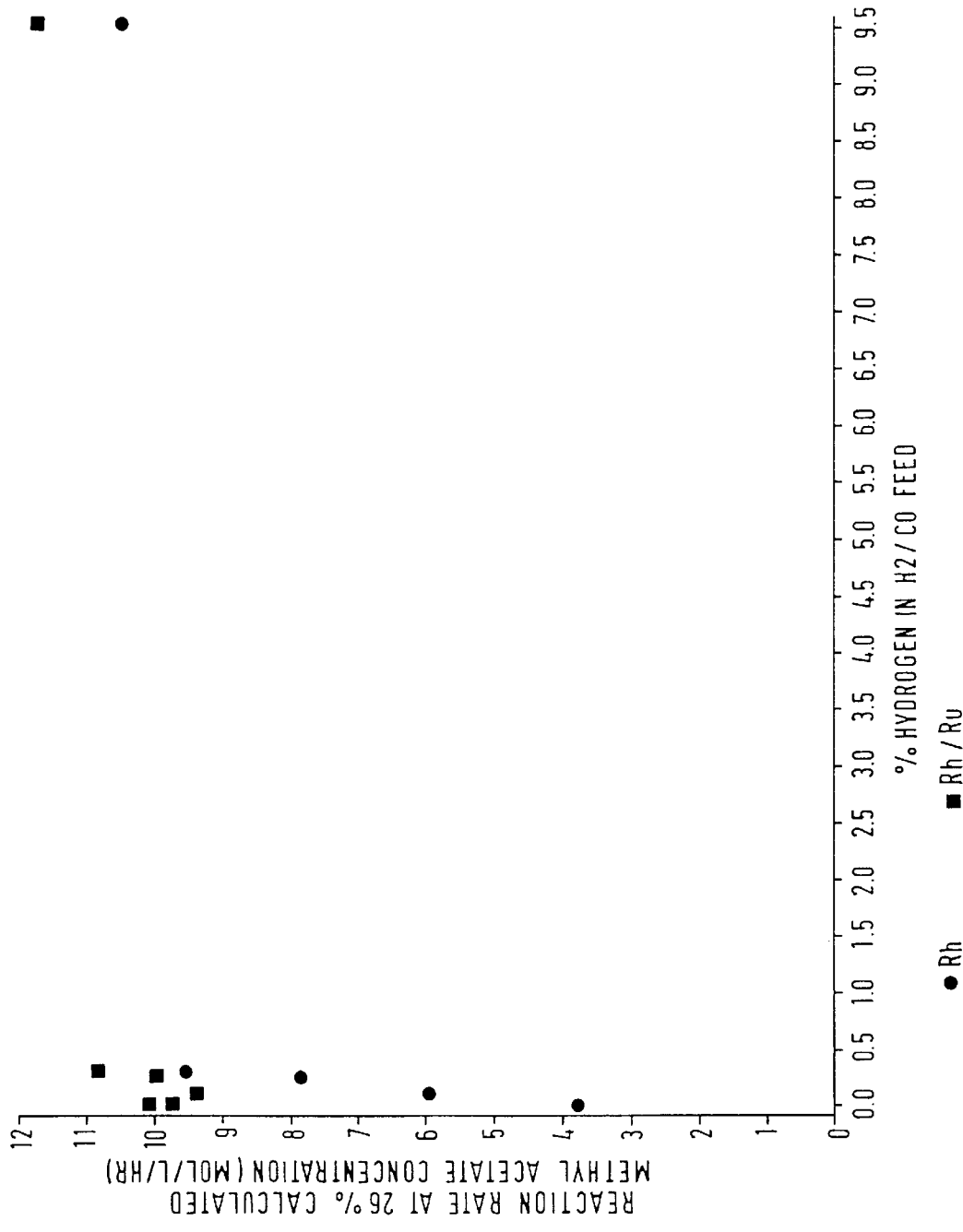

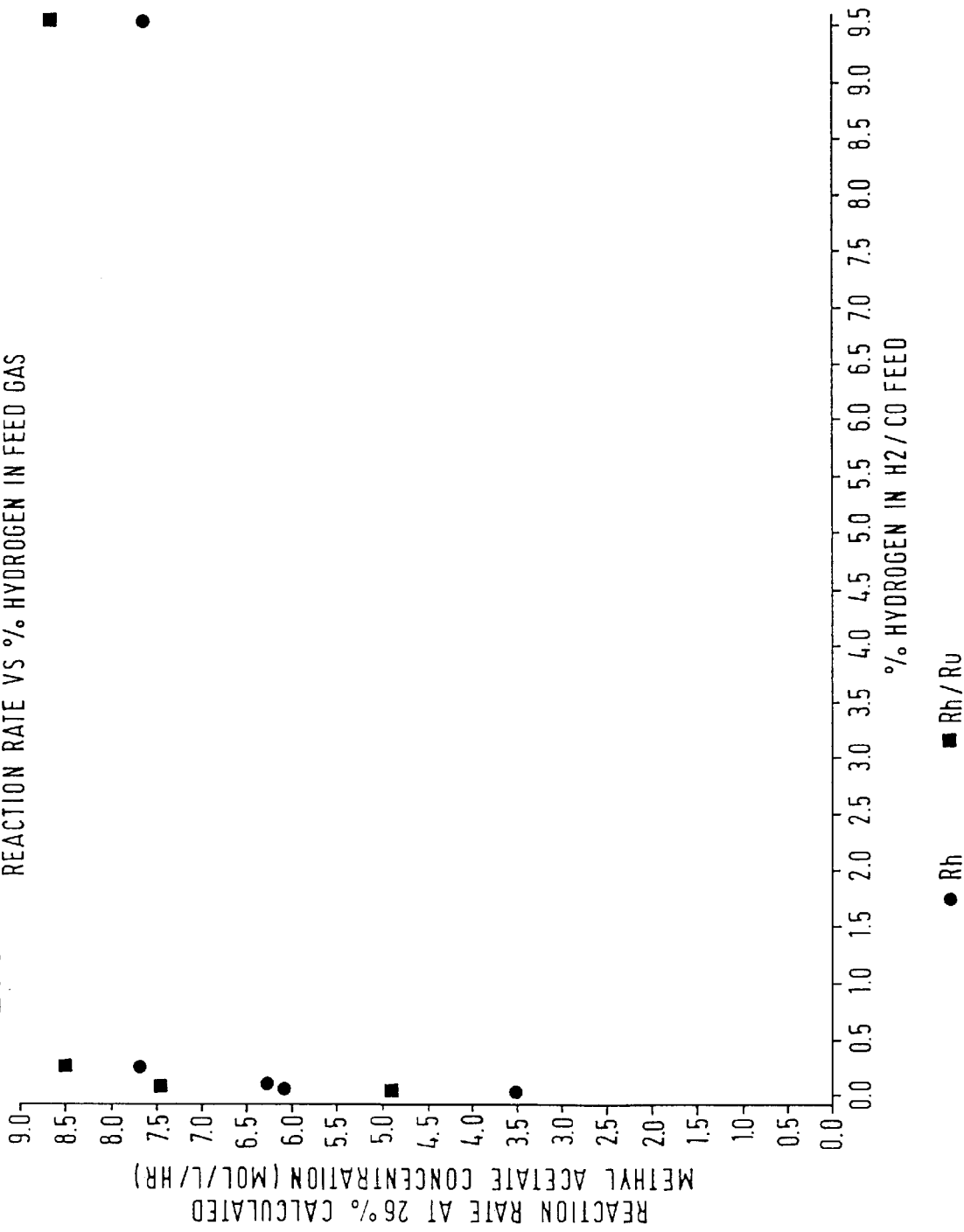

PROCESS FOR THE CARBONYLATION OF AN ALCOHOL

This application is a continuation of application Ser. No. 08/458,442, filed Jun. 2, 1995 now abandoned.

The present invention relates to a carbonylation process and in particular to a process for the carbonylation of a $C_1$ to $C_4$ alcohol and/or a reactive derivative thereof in the presence of a rhodium catalyst and an alkyl halide.

Carbonylation processes in the presence of rhodium catalysts are known and are described, for example, in U.S. Pat. No. 3,769,329, GB 1468940, GB 1538783 and EP 0087070.

Carbonylation processes in the presence of ruthenium and osmium catalysts are also known. Thus, UK patent GB 1234641 describes a process for the production of an organic acid or an ester by carbonylation of an alcohol, halide, ester, ether or phenol in the presence of a noble metal catalyst selected from iridium, platinum, palladium, osmium and ruthenium and their compounds and a promoter which is a halogen or halogen compound.

According to Jenner et al in J. Mol. Catalysis 40 (1987) 71–82 ruthenium compounds are effective carbonylation catalysts for converting primary alcohols into acids and esters at high CO pressures. In the reported experiments standard conditions were 450 bar CO pressure and low CO pressures were said to lead to high yields of hydrocarbons and a lower yield of ester.

UK patent application GB 2029409 describes a process for the preparation of aliphatic carboxylic acids and esters by reacting carbon monoxide with alcohols at an elevated pressure of 34 atmospheres or greater in the presence of a ruthenium catalyst and halogen-containing promoter.

U.S. Pat. No. 4,046,807 relates to a process for preparing acetic anhydride from acetic acid methyl ester and carbon monoxide in the presence of a Group VIII noble metal catalyst selected from ruthenium, rhodium, palladium, osmium, iridium and platinum.

The technical problem to be solved is to provide an improved process for the carbonylation of a $C_1$ to $C_4$ alkyl alcohol and/or a reactive derivative thereof in the presence of a rhodium catalyst and alkyl halide.

Thus, according to the present invention there is provided a process for the carbonylation of a $C_1$ to $C_4$ alkyl alcohol and/or a reactive derivative thereof which process comprises contacting a $C_1$ to $C_4$ alkyl alcohol and/or a reactive derivative thereof with carbon monoxide in a liquid reaction composition in a carbonylation reactor characterised in that the liquid reaction composition comprises: (a) a rhodium catalyst, (b) an alkyl halide, and (c) as promoter, at least one of ruthenium and osmium.

The carbonylation product of the present invention comprises the corresponding carboxylic acid, alkyl ester and/or carboxylic acid anhydride. Thus, the corresponding carboxylic acid product of an alkyl alcohol having n carbon atoms is a carboxylic acid having n+1 carbon atoms. The corresponding ester product of an alkyl alcohol having n carbon atoms is an ester of a carboxylic acid having n+1 carbon atoms with the alcohol reactant. The corresponding carboxylic acid anhydride product of an alkyl alcohol having n carbon atoms is the anhydride of the carboxylic acid having n+1 carbon atoms. Preferably, acetic acid, methyl acetate and/or acetic anhydride are produced in the process of the present invention by the carbonylation of methanol and/or a reactive derivative thereof. Preferably, methanol and/or methyl acetate are used as reactants. Acetic acid may be produced using the process of the present invention by the carbonylation of methanol and/or reactive derivatives of methanol including methyl acetate, dimethyl ether and methyl iodide. Acetic anhydride may be produced in the process of the present invention by the carbonylation, under substantially anhydrous conditions, of methyl acetate and/or dimethyl ether optionally with methanol and/or water present in the reactant feed to the reactor.

Carboxylic acid may be produced as a carbonylation product of the process of the present invention when at least a finite concentration of water is present in the liquid reaction composition that is at least 0.1% by weight. The water may be formed in situ in the liquid reaction composition, for example, by the esterification reaction between alcohol reactant and carboxylic acid product. Also, water may be introduced to the carbonylation reactor together with or separately from other components of the liquid reaction composition. Water may be separated from other components of the reaction composition withdrawn from the reactor and may be recycled in controlled amounts to maintain the concentration of water in the liquid reaction composition. Suitably, the water concentration in the liquid reaction composition is in the range 0.1 to 15% by weight. Preferably, the concentration of water in the liquid reaction composition is maintained below 14% by weight, more preferably below 11% by weight, most preferably below 7% by weight.

Carboxylic anhydride may be produced as the carbonylation product of the process of the present invention optionally with carboxylic acid by ensuring that the liquid reaction composition is maintained under substantially anhydrous conditions. By substantially anhydrous conditions is meant the complete absence of water or less than 0.1% by weight water in the liquid reaction composition in the carbonylation reactor.

At least some of the alcohol and/or reactive derivative thereof will be converted to, and hence present as, corresponding ester in the liquid reaction composition by reaction with carboxylic acid product or solvent. Any suitable concentration of ester in the liquid reaction composition may be used, for example in the range from 0.1% to 50% by weight, preferably up to about 35% by weight. Thus, for example, in a continuous process for the preparation of acetic acid by carbonylation of methanol and/or a reactive derivative thereof in the presence of water, the concentration of methyl acetate in the liquid reaction composition may typically be up to 5% by weight whilst in a continuous process for the preparation of acetic anhydride by carbonylation of methanol and/or a reactive derivative thereof under substantially anhydrous conditions, the concentration of methyl acetate in the liquid reaction composition may typically be in the range 15 to 30% by weight.

It has been found that as water concentration in the liquid reaction composition is decreased it is preferred to increase the ester concentration. Thus for example in a process for preparation of acetic acid at a water concentration of 5.7% by weight the methyl acetate concentration is preferably greater than 1.2% by weight and at a water concentration of 2.5% by weight the methyl acetate concentration is preferably greater than 2% by weight.

The rhodium catalyst in the liquid reaction composition may comprise any rhodium containing compound which is soluble in the liquid reaction composition. The rhodium catalyst may be added to the liquid reaction composition in any suitable form which dissolves in the liquid reaction composition or is convertible to a soluble form. Examples of suitable rhodium-containing compounds which may be added to the liquid reaction composition include [Rh(CO)

$_2Cl]_2$, [Rh(CO)$_2$I]$_2$, [Rh(Cod)Cl]$_2$, rhodium (III) chloride, rhodium (III) chloride trihydrate, rhodium (III) bromide, rhodium (III) iodide, rhodium (III) acetate, rhodium dicarbonylacetylacetonate, RhCl$_3$(PPh$_3$)$_3$ and RhCl(CO)(PPh$_3$)$_2$.

Preferably, the rhodium catalyst concentration in the liquid reaction composition is in the range 50 to 5000 ppm by weight of rhodium, preferably 100 to 1500 ppm.

The ruthenium and/or osmium promoter may comprise any ruthenium and/or osmium containing compound which is soluble in the liquid reaction composition. The promoter may be added to the liquid reaction composition for the carbonylation reaction in any suitable form which dissolves in the liquid reaction composition or is convertible to soluble form. The promoter compound may be used as chloride free compounds such as acetates which are soluble in one or more of the liquid reaction composition components, for example water and/or acetic acid and so may be added to the reaction as solutions therein.

Examples of suitable ruthenium-containing compounds which may be used include ruthenium (III) chloride ruthenium (III) chloride trihydrate, ruthenium (IV) chloride, ruthenium (III) bromide, ruthenium (III) iodide ruthenium metal, ruthenium oxides, ruthenium (III) formate, [Ru(CO)$_3$I$_3$]$^-$H$^+$, tetra(aceto)chlororuthenium(II,III), ruthenium (III) acetate, ruthenium (III) propionate, ruthenium (III) butyrate, ruthenium pentacarbonyl, triruthemiumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis(4-cymene)diruthenium(II), tetraclilorobis(benzene)diruthenium(II), dichloro(cycloocta-1,5-diene)ruthenium (II) polymer and tris(acetylacetonate) ruthenium (III).

Examples of suitable osmium containing compounds which may be used include osmium (III) chloride hydrate and anhydrous, osmium metal, osmium tetraoxide, triosmiumdodecacarbonyl, pentachloro-p-nitrododiosmium and mixed osmium halocarbonyls such as tricarbonyldichloroosmium (II) dimer and other organoosmium complexes.

In the production of acetic anhydride by carbonylation of methyl acetate with optional methanol in the process of the present invention in batch autoclave experiments, which last for only about 20 minutes, it was found that ruthenium (III) trichloride and osmium (III) trichloride were not suitable sources of promoter unless hydrogen is also present with the carbon monoxide feed gas. Without wishing to be bound by any theory it is believed that, when acetic anhydride is produced using the process of the present invention, the promoter is preferably added to the liquid reaction composition in a low oxidation state form or is converted into a low oxidation state form in situ in the liquid reaction composition. Thus, these precursors may be converted to a suitable form over longer time periods, for example, in a continuous carbonylation process wherein catalyst is continuously recycled between the carbonylation reactor and a product recovery section.

The molar ratio of each promoter: rhodium catalyst is suitably in the range 0.1:1 to 20:1, preferably 1:1 to 10:1. It is further preferred, when the process of the present invention is performed with a substantially anhydrous liquid reaction composition that the molar ratio of each promoter::rhodium is about 1:1.

Preferably, the alkyl halide has an alkyl moiety which is the same as the alkyl moiety of the reactant and is more preferably methyl. Preferably, the alkyl halide is an iodide or bromide, most preferably an iodide. Preferably, the concentration of alkyl halide in the liquid reaction composition is in the range 1 to 30% by weight, preferably 1 to 20%, more preferably 5 to 20% by weight.

The carbon monoxide reactant may be essentially pure or may contain inert impurities such as carbon dioxide, methane, nitrogen, noble gases, water and $C_1$ to $C_4$ paraffinic hydrocarbons.

The presence of hydrogen in the carbon monoxide feed and generated in situ by the water gas shift reaction is preferably kept low, for example, less than 2 bar partial pressure, as its presence may result in the formation of hydrogenation products. Whilst increasing the partial pressure of hydrogen in a carbonylation process performed under substantially anhydrous conditions may increase the rate of reaction, a disadvantage is that it also increases the formation of by-products. An advantage of the present invention is that the presence of a promoter such as ruthenium enables the rate of reaction to be maintained at lower partial pressure of hydrogen than would otherwise be required without the promoter. This has the advantage of reducing by-product formation whilst maintaining rate of reaction. Thus, for example, the promoters of the present invention may allow the hydrogen partial pressure in a continuous process for the production of acetic anhydride to be reduced from a partial pressure in the range 0.6 to 1 bar to a partial pressure up to 0.5 (suitably 0.05 to 0.5 bar) whilst maintaining rate of reaction and reducing by-product formation. Preferably, the ratio of carbon monoxide to hydrogen is greater than 10:1 molar in the reactor. The partial pressure of carbon monoxide in the reaction is suitably in the range 1 to 70 bar, preferably 1 to 45 bar, more preferably 1 to 35 bar. A suitable carbon monoxide partial pressure for production of acetic anhydride is about 20 to 30 bar and a suitable carbon monoxide partial pressure for production of acetic acid in the presence of water is less than 15 bar.

The catalyst system of the present invention has been found to be particularly beneficial for the production of carboxylic acid such as acetic acid at relatively low partial pressures of carbon monoxide where the rate of reaction may be limited by the amount of carbon monoxide in solution in the liquid reaction composition. Under these conditions, it has been found that the catalyst system of the present invention has the advantage of providing an increased rate of carbonylation reaction over catalyst systems without the promoters of the present invention. This advantage allows for increased rate of reaction under conditions when the carbon monoxide partial pressure is relatively low, for example less than 5 bar, for example due to a low total pressure in the carbonylation reactor or due to high vapour pressure of components of the liquid reaction composition, for example at high ester concentration in the liquid reaction composition or due to a high concentration of inert gases (for example nitrogen and carbon dioxide) in the carbonylation reactor. The catalyst system may also have advantages of increasing rate of carbonylation when the rate of reaction is reduced by the availability of carbon monoxide in solution in the liquid reaction composition resulting from mass transfer limitations, for example due to poor agitation.

A further advantage of the catalyst system of the present invention is that the ruthenium or osmium promoter acts as a stabiliser for the rhodium catalyst at relatively low partial pressures of carbon monoxide for example less than 0.25 bar, for example during recovery of carbonylation product from the reaction composition with the recycle of the catalyst to the carbonylation reaction.

Yet a further advantage of the catalyst system of the present invention is the improved carbonylation rate over rhodium alone, which is obtained under low water concentrations in the production of carboxylic acids, for example, at less than 7% by weight water in the reaction composition during the production of acetic acid.

The pressure of the carbonylation reaction is suitably in the range 1 to 100 barg, preferably 20 to 50 barg. The temperature of the carbonylation reaction is suitably in the range 130 to 250° C., preferably in the range 170 to 200° C.

Co-promoters including Group IA metal iodides, quaternary ammonium iodides and phosphonium iodides may be present in the liquid reaction composition. Such co-promoters will reduce the formation of volatile promoter species and so facilitate product recovery and purification. When carboxylic acid, such as acetic acid, is the product of the carbonylation reaction in the presence of a finite concentration of water, the concentration of co-promoter in the liquid reaction composition is preferably equivalent, on a molar basis, to less than about 3% by weight of lithium iodide. When carboxylic anhydride such as acetic anhydride is produced in the carbonylation reaction, the concentration of a co-promoter in the liquid reaction composition is preferably present at up to its limit of solubility, for example up to 30% by weight iodide as N,N' dimethyl imidazolium iodide or lithium iodide.

Carboxylic acid and/or carbonylation anhydride may be used as a solvent for the reaction.

The process of the present invention may be performed as a batch or a continuous process, preferably as a continuous process.

Carboxylic acid, ester and/or carboxylic anhydride carbonylation products may be removed from the reactor by withdrawing liquid reaction composition and separating the acid, ester and/or acetic anhydride product by one or more flash and/or fractional distillation stages from the other components of the liquid reaction composition such as rhodium catalyst, ruthenium and/or osmium promoter, alkyl halide, water (if present) and unconsumed reactants which may be recycled to the reactor to maintain their concentrations in the liquid reaction composition. Such separation generally takes place at a carbon monoxide partial pressure less than in the carbonylation reactor. The acid, ester and/or anhydride product may also be removed as a vapour from the reactor.

BRIEF DESCRIPTION OF DRAWINGS

The invention will now be illustrated by way of example only by reference to the following examples and to FIGS. 1 to 6 in which

FIGS. 5 and 6 represent graphs showing the effect of hydrogen concentration in the feedgas on reaction rate for anhydrous carbonylation.

Figure 1:
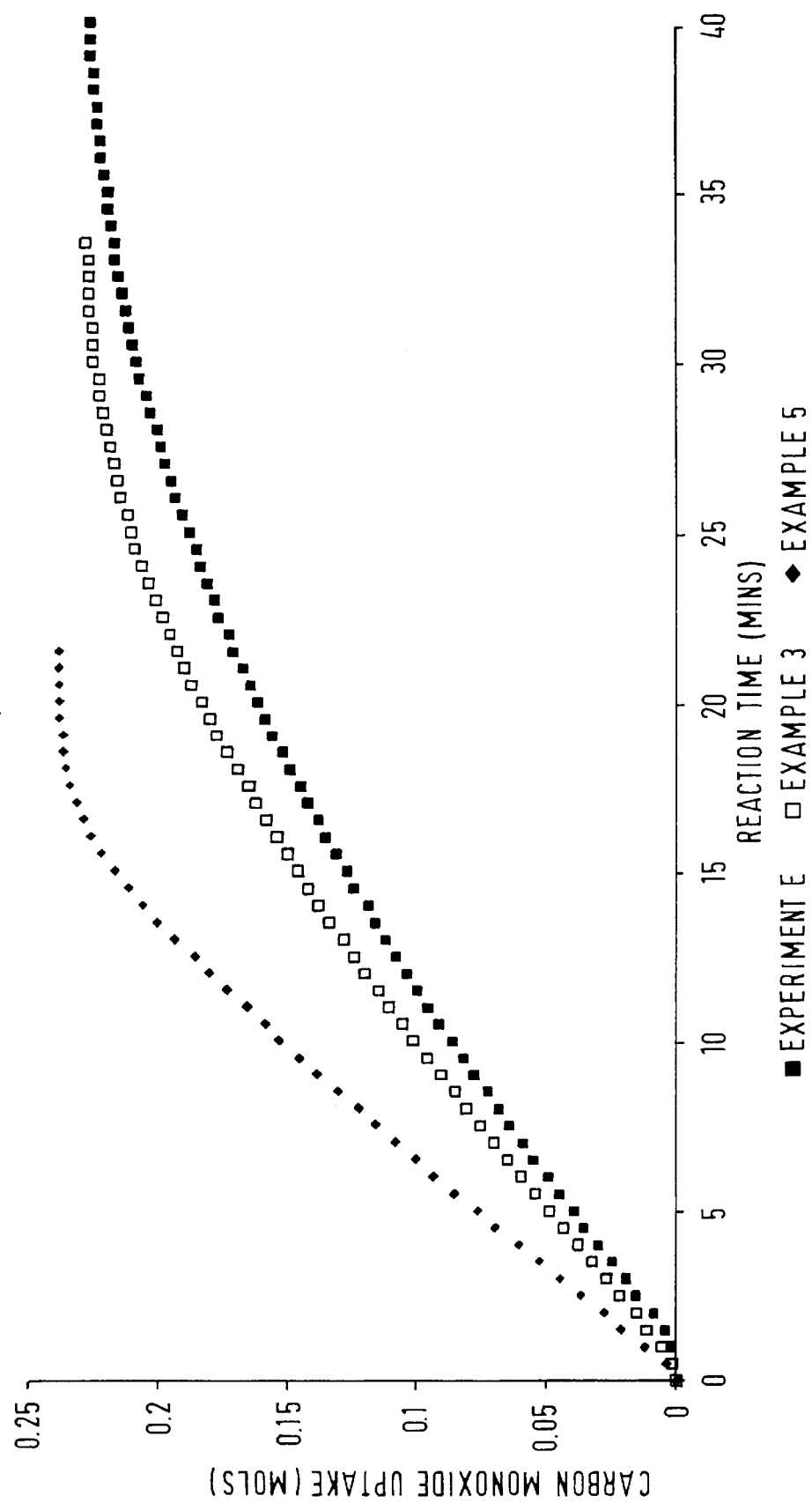
FIG. 1 represents a graph of carbon monoxide uptake against reaction time for Experiment E and Examples 3 and 5.

In the examples reaction rates are quoted as number of moles of product/reactant produced/consumed per liter of cold degassed reactor composition per hour (mol/l/hr).

In the examples the concentration of components and in particular of water and methyl acetate, during the carbonylation reaction was calculated from the starting composition, assuming that one mole of water is consumed for every mole of carbon monoxide that is consumed. No allowance was made for the organic components in the autoclave headspace.

A 150 ml Hastelloy B2 (Trade Mark) autoclave equipped with a Magnedrive (Trade Mark) stirrer and liquid injection facility was used for a series of batch carbonylation experiments. A gas supply to the autoclave was provided from a gas ballast vessel, feed gas being provided to maintain the autoclave at a constant pressure and the rate of gas uptake being calculated (with an accuracy believed to be ±1%) from the rate at which the pressure falls in the gas ballast vessel.

At the end of each experiment liquid and gas samples from the autoclave were analysed by gas chromatography.

For each batch carbonylation experiment the autoclave was charged with the ruthenium or osmium promoter and the liquid components of the liquid reaction composition excluding part of the acetic acid charge, in which the rhodium catalyst was dissolved.

The autoclave was flushed twice with nitrogen and once with carbon monoxide and was then heated with stirring (1000 rpm) to 185° C. After allowing the system to stabilise at autogeneous pressure for about 30 minutes, the rhodium catalyst in acetic acid solution was then injected into the autoclave under pressure of carbon monoxide. The pressure in the autoclave was subsequently maintained at 27 barg with carbon monoxide fed on demand from the gas ballast vessel through the liquid injection facility.

After an initial 30 seconds to allow for carbon monoxide to dissolve in the reaction composition, subsequent gas uptake from the ballast vessel was measured every 30 seconds and from this was calculated the rate of carbonylation, expressed as moles of carbon monoxide per liter of liquid reaction composition per hour (mol/l/hr). After uptake of carbon monoxide from the ballast vessel had ceased or the reaction had proceeded for a period of 40 minutes, whichever was sooner, the autoclave was isolated from the gas supply. The contents of the autoclave were cooled to room temperature and the gases were cautiously vented from the autoclave, sampled and analysed. The liquid reaction composition was discharged from the autoclave, sampled and was analysed for liquid products and by-products.

To obtain a reliable baseline a number of identical baseline runs may have to be performed to condition the autoclave such that consistent rates are achieved. This conditioning period is often different from autoclave to autoclave and may depend upon its previous history.

Experiment A

A baseline experiment was performed with the autoclave charged with methyl acetate (244 mmol), water (912 mmol), methyl iodide (101 mmol), and acetic acid (703 mmol). The rhodium catalyst solution comprised $Rh_2(CO)_4Cl_2$ (0.19 mmol) dissolved in acetic acid (83 mmol). The reaction was performed at a constant pressure of 27 barg and at a temperature of 185° C.

The rate of reaction, based upon carbon monoxide uptake, remained constant at 8.2 mol/l/hr until a calculated water concentration of 12.1% by weight was reached. At this point the methyl acetate reactant was virtually all consumed. High conversion to acetic acid was observed. Traces of acetaldehyde by-product were detected in the liquid reaction composition at the end of the experiment. The non-condensable gases vented at the end of the experiment were analysed. This analysis did not determine hydrogen but included nitrogen and carbon monoxide. The compositions are expressed as a volume percentage of the measureable gases and were found to contain 2.7% carbon dioxide and methane (traces), the balance comprising carbon monoxide.

This is not an example according to the present invention because no ruthenium or osmium promoter was present in the liquid reaction composition.

Experiment B

Experiment A was repeated. The reaction rate, measured in an identical manner to Experiment A was 8.8 mol/l/hr.

The vented gas at the end of the experiment was analysed as in Experiment A and was found to contain 3.4% carbon dioxide and methane (trace).

EXAMPLE 1

Experiment A was repeated except that $RuI_3$ (3.96 mmol) was charged to the autoclave at the start before the rhodium catalyst solution was added.

The rate of reaction, based upon carbon monoxide uptake, remained constant at 8.3 mol/l/hr until a calculated water concentration of 11.9% by weight was reached. This rate is, within experimental error, the same as the rates measured in Experiments A and B. This example shows that at the conditions of this example of high water concentrations there is no measurable benefit of the presence of ruthenium in the liquid reaction composition on the carbonylation rate. Subsequent experiments show that as the water concentration is reduced the benefit to a reaction rate becomes measurable.

Experiment D

A baseline experiment was performed at a lower water concentration than those employed in Examples A and B. The autoclave was charged with methyl acetate (244 mmol), water (556 mmol), methyl iodide (102 mmol), and acetic acid (809 mmol). The rhodium catalyst solution comprised $Rh_2(CO)_4Cl_2$ (0.20 mmol) dissolved in acetic acid (83 mmol). The reaction was performed at a constant pressure of 27 barg and at a temperature of 185° C.

The rate of reaction, based upon carbon monoxide uptake, remained constant at 8.06 mol/l/hr, until a calculated water concentration of 6.8% by weight was reached. Acetic acid was the major (>99%) liquid product detected. The measurable, non-condensable gases in the autoclave at room temperature at the end of the reaction were analysed as before and were found to contain by volume, 1.3% carbon dioxide and methane (trace), the balance comprising carbon monoxide.

This is not an example according to the present invention because no ruthenium or osmium promoter was present in the liquid reaction composition.

EXAMPLE 2

Experiment D was repeated except that $RuI_3$ (3.95 mmol) was charged to the autoclave at the start before the rhodium catalyst solution was added.

The rate of reaction, based upon carbon monoxide uptake, remained constant at 7.4 mol/l/hr, until a calculated water concentration of 6.0% by weight was reached. The reaction was allowed to proceed to completion and subsequent analysis of the liquid reaction composition revealed acetic acid to be the major (>99%) product. The measurable, non-condensable gases, analysed as before, contained 2.7% carbon dioxide, 0.4% methane and carbon monoxide (balance).

This Example is according to the present invention and demonstrates the benefit of the presence of ruthenium in the liquid reaction composition of maintaining the carbonylation rate down to a water concentration of at least as low as 6.0% by weight. Subsequent examples illustrate maintenance of rate to even lower water concentrations.

Experiment E

A baseline experiment was performed at lower water concentrations than those employed in Experiment D. The autoclave was charged with methyl acetate (244 mmol), water (272 mmol), methyl iodide (101 mmol), and acetic acid (894 mmol). The rhodium catalyst solution comprised $Rh_2(CO)_4Cl_2$ (0.20 mmol) dissolved in acetic acid (83 mmol). The reaction was performed at a constant pressure of 27 barg and at a temperature of 185° C.

The rate of reaction, based upon carbon monoxide uptake, did not remain constant but was found to decrease from an initial rate of 6.9 mol/l/hr, until the reaction was stopped after 40 minutes (see FIG. 1 which represents carbon monoxide uptake against reaction time). Acetic acid was the major (>99%)observed product.

The non-condensable gases measured as before, contained carbon dioxide (trace) and carbon monoxide (balance).

This is not an example according to the present invention because no ruthenium or osmium promoter was present in the liquid reaction composition.

EXAMPLE 3

Experiment E was repeated except that $RuCl_3.3H_2O$ (0.39 mmol) was charged to the autoclave at the start before the rhodium catalyst solution was added.

The rate of reaction, based upon carbon monoxide uptake rate, remained constant at 6.8 mol/l/hr until a calculated water concentration of 2.8% by weight was reached (see FIG. 1). The reaction was allowed to proceed to completion and subsequent analysis of the liquid reaction composition showed acetic acid to be the major (>99%) product, although traces of methyl chloride (not quantified) were also detected. The non-condensable gases, measured as before, contained carbon dioxide (trace) and carbon monoxide (balance).

This Example is according to the present invention and demonstrates that the presence of ruthenium in the liquid reaction composition allows the reaction rate to remain constant at low water concentrations.

EXAMPLE 4

Example 3 was repeated except that $RuCl_3.3H_2O$ (1.94 mmol), methyl acetate (244 mmol), water (270 mmol), methyl iodide (102 mmol), and acetic acid (895 mmol) were charged to the autoclave.

The rate of reaction, based upon carbon monoxide uptake, remained constant at 8.8 mol/l/hr until a calculated water concentration of 1.7% by weight was reached. The reaction was allowed to proceed until completion and subsequent analysis of the liquid reaction composition showed acetic acid to be the major (>99%) product, although traces of methyl chloride (not quantified) were also detected. The non-condensable gases, measured as before, contained carbon dioxide (trace) and carbon monoxide (balance).

This Example is according to the present invention and shows the benefit of an increase in the concentration of ruthenium in the liquid reaction composition on the carbonylation rate by allowing the rate of reaction to remain constant at low water concentrations.

EXAMPLE 5

Example 3 was repeated except that $RuCl_3.3H_2O$ (3.92 mmol), methyl acetate (244 mmol), water (267 mmol), methyl iodide (102 mmol), and acetic acid (894 mmol) were charged to the autoclave.

Figure 2:
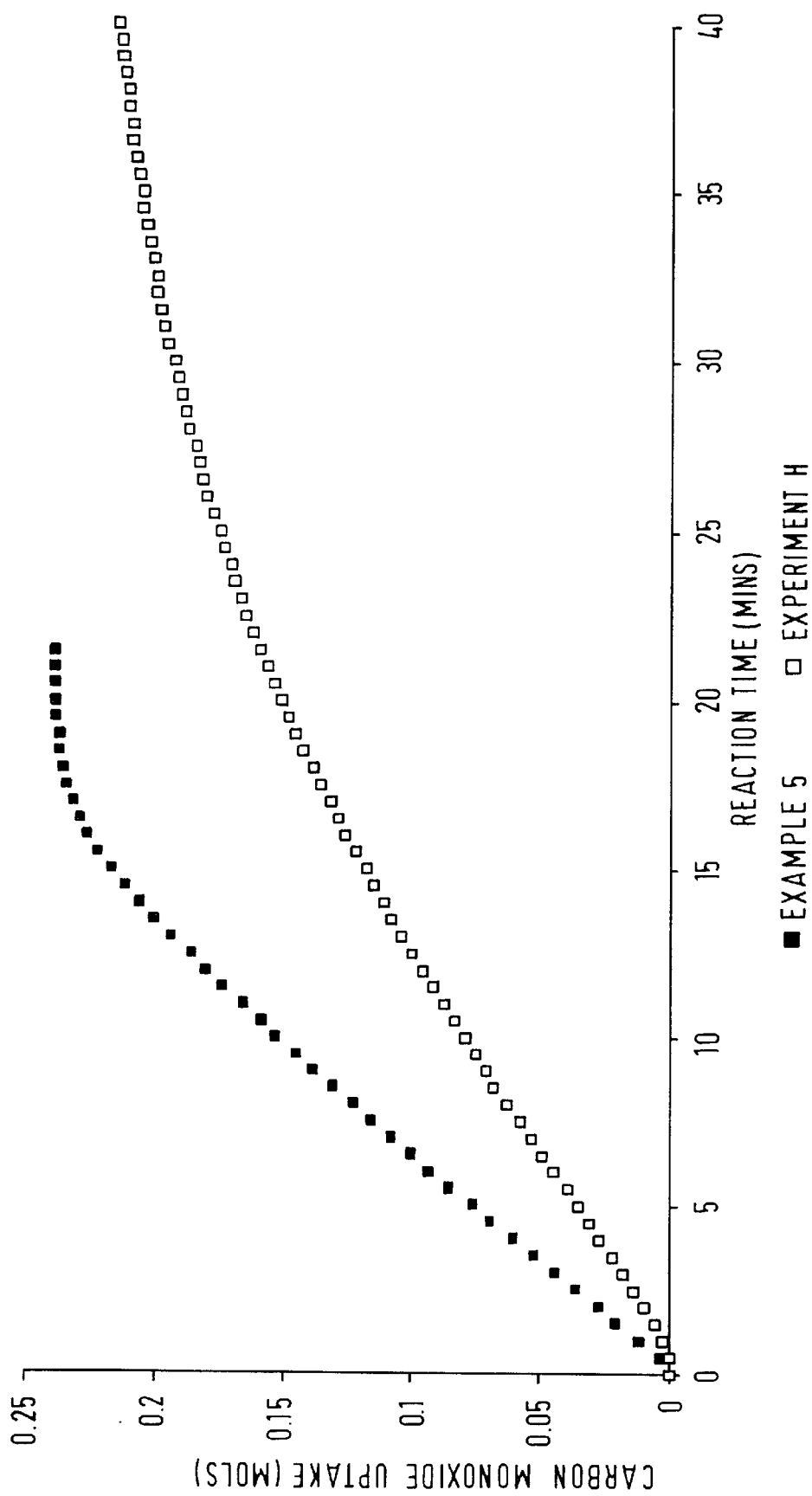
FIG. 2 represents a graph of carbon monoxide uptake against reaction time for Example 5 and Experiment H.

The rate of reaction, based upon carbon monoxide uptake, remained constant at 10.4 mol/l/hr until a calculated water concentration of 1.6% by weight was reached (see FIGS. 1 and 2). The reaction was allowed to proceed to completion and subsequent analysis of the liquid reaction composition showed acetic acid to be the major (>99%) product, although traces of methyl chloride (not quantified) were also detected. The non-condensable gases, measured as before, contained carbon dioxide (trace) and carbon monoxide (balance).

This Example is according to the present invention and shows the benefit of a further increase in the concentration of ruthenium in the liquid reaction composition by allowing the rate of reaction to remain constant at low water concentrations.

Figure 3:
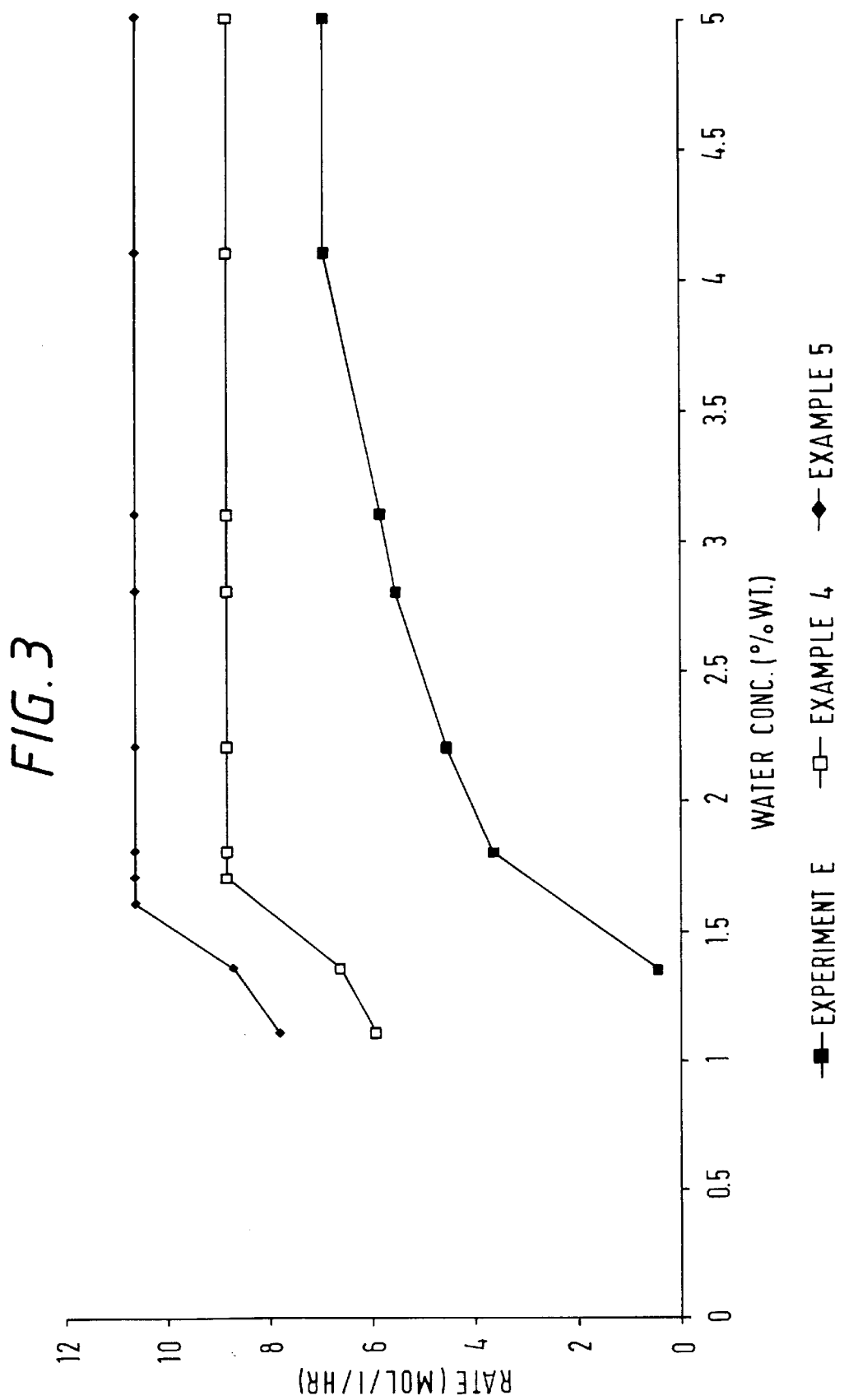
FIG. 3 represents a graph showing the effect of ruthenium promoter on reaction rate against calculated water concentration.

The results of Examples 4, 5 and Experiment E are shown in graph form in FIG. 3 as the rate of reaction against calculated water concentration. This shows the benefit of ruthenium of maintaining reaction rate as water concentration decreases during the course of the batch reaction. Similar effects would be expected in continuously operated reactors.

EXAMPLE 6

Experiment E was repeated except that osmium trichloride hydrate (1.69 mmol) was charged to the autoclave at the start before the rhodium catalyst solution was added.

The rate of reaction, based upon carbon monoxide uptake, remained constant at 7.3 mol/l/hr until a calculated water concentration of 2.3% by weight was reached. The reaction rate then decreased as the reaction was allowed to proceed to completion. The major (>99%) liquid product was acetic acid although traces of methyl chloride (not quantified) were detected. The non-condensable gases measured as before, contained carbon dioxide (1.1%) and carbon monoxide (balance).

This example is according to the present invention and shows the benefit of the presence of osmium in the liquid reaction composition on the reaction rate.

Experiment F

The autoclave was charged with methyl acetate (244 mmol), water (270 mmol), methyl iodide (101 mmol), acetic acid (978 mmol) and $RuCl_3.3H_2O$ (3.63 mmol). No rhodium catalyst solution was added to the autoclave. The autoclave was heated at 185° C. at a constant pressure of 28 bar, for about 1 hour but no uptake of carbon monoxide gas from the ballast vessel was observed.

The amount of methyl acetate in the liquid reaction composition at the end of the experiment was measured to be 226 mmol (this may be subject to some degree of calibration error at this high level). The non-condensable gases measured as before, contained carbon dioxide (trace) and carbon monoxide (balance).

This is not an example according to the present invention because no rhodium catalyst was present in the liquid reaction composition. This example shows that ruthenium alone did not act as a catalyst for the carbonylation of methyl acetate.

Experiment G

Experiment F was repeated except that osmium trichloride hydrate (1.69 mmol) rather than ruthenium trichloride trihydrate was charged to the reactor. The amount of methyl acetate in the liquid reaction composition at the end of the experiment was measured to be 233 mmol (this is subject to some degree of calibration error at this high level). The non-condensable gases measured as before, contained carbon dioxide (trace) and carbon monoxide (balance). This is not an example according to the present invention because no rhodium catalyst was present in the liquid reaction composition. This experiment shows that osmium alone did not act as a catalyst for the carbonylation of methyl acetate.

Experiment H

The autoclave was charged with methyl acetate (244 mmol), water (271 mmol), methyl iodide (101 mmol), acetic acid (894 mmol) and lithium iodide (3.81 mmol). The rhodium catalyst solution comprised $Rh_2(CO)_4Cl_2$ (0.20 mmol) dissolved in acetic acid (83 mmol). The reaction was performed at a constant pressure of 27 barg and at a temperature of 185° C.

The rate of reaction, based upon carbon monoxide uptake, did not remain constant but was found to decrease from an initial rate of 6.8 mol/l/hr, until the reaction was stopped after 40 minutes (see FIG. 2). The major (>99%) observed liquid product was acetic acid. The non-condensable gases, measured as before, contained carbon dioxide (trace) and carbon monoxide (balance).

This is not an example according to the present invention because no ruthenium or osmium promoter was present in the liquid reaction composition. This experiment demonstrates that addition of lithium iodide to the liquid reaction mixture does not allow the rate of reaction to remain constant at low water concentrations.

Examples at Low Carbon Monoxide Partial Pressure

A series of batch carbonylation experiments were performed using the procedure described above except that the autoclave was flushed twice with nitrogen, and was then heated with stirring (1000 rpm) to 185° C., On attaining a temperature of 185° C., nitrogen was introduced into the autoclave to achieve a desired pressure which pressure was less than the final reaction pressure. The gas feed lines to the autoclave were then vented and flushed with carbon monoxide. The pressure in the autoclave was subsequently maintained at a set pressure in the range 27 and 28 barg with carbon monoxide fed on demand from the gas ballast vessel through the liquid injection facility. The partial pressure of carbon monoxide employed in the experiment was then simply calculated by subtracting the pressure when nitrogen was introduced to the autoclave at 185° C. from the final reaction pressure. The measurement of gas uptake was as described above.

Experiment I

A baseline experiment was performed with the autoclave charged with methyl acetate (244 mmol), water (911 mmol), methyl iodide (102 mmol), and acetic acid (706 mmol). The rhodium catalyst solution comprised $Rh_2(CO)_4Cl_2$ (0.19 mmol) dissolved in acetic acid (83 mmol). The reaction was performed at a constant pressure of 27.5 barg with a partial pressure of carbon monoxide of 6.3 bar, and at a temperature of 185° C.

The rate of reaction, based upon carbon monoxide uptake rate, after 5 minutes, was calculated to be 6.4 mol/l/hr. High conversion to acetic acid was observed. Traces of acetaldehyde by-product were detected in the liquid reaction composition at the end of the experiment. The non-condensable gases, measured as before, contained carbon dioxide (3.7%), methane (2.1%) and carbon monoxide (balance).

This is not an example according to the present invention because no ruthenium or osmium promoter was present in the liquid reaction composition.

EXAMPLE 7

Experiment I was repeated except that $RuCl_3$ (3.96 mmol) was charged to the autoclave at the start before the rhodium catalyst solution was added. The reaction pressure was maintained at 27.3 barg, the partial pressure of carbon monoxide being 5.9 bar.

The rate of reaction, based upon carbon monoxide uptake rate, after 5 minutes was calculated to be 5.0 mol/l/hr. High conversion to acetic acid was observed. Traces of acetaldehyde by-product were detected in the liquid reaction composition at the end of the experiment. The non-condensable gases, measured as before, contained carbon dioxide (6.4%), methane (6.9%) and carbon monoxide (balance). The difference between the rate measured in this experiment and the rate measured in Experiment I is not considered significant when the slight differences in carbon monoxide partial pressure are also taken into consideration.

This example shows that when ruthenium was present in the liquid reaction composition of this experiment at relatively high carbon monoxide partial pressure and relatively high water concentration, there is no measurable benefit on reaction rate. Subsequent experiments show at lower partial pressure of carbon monoxide there is a benefit on reaction rate.

Experiment K

Experiment I was repeated except that the autoclave was charged with methyl acetate (244 mmol), water (911 mmol), methyl iodide (101 mmol), and acetic acid (704 mmol), and the reaction was performed at 185° C.; a total pressure of 27.4 barg and at a carbon monoxide partial pressure of 4.8 bar (0.20 mol of catalyst was used).

Figure 4:
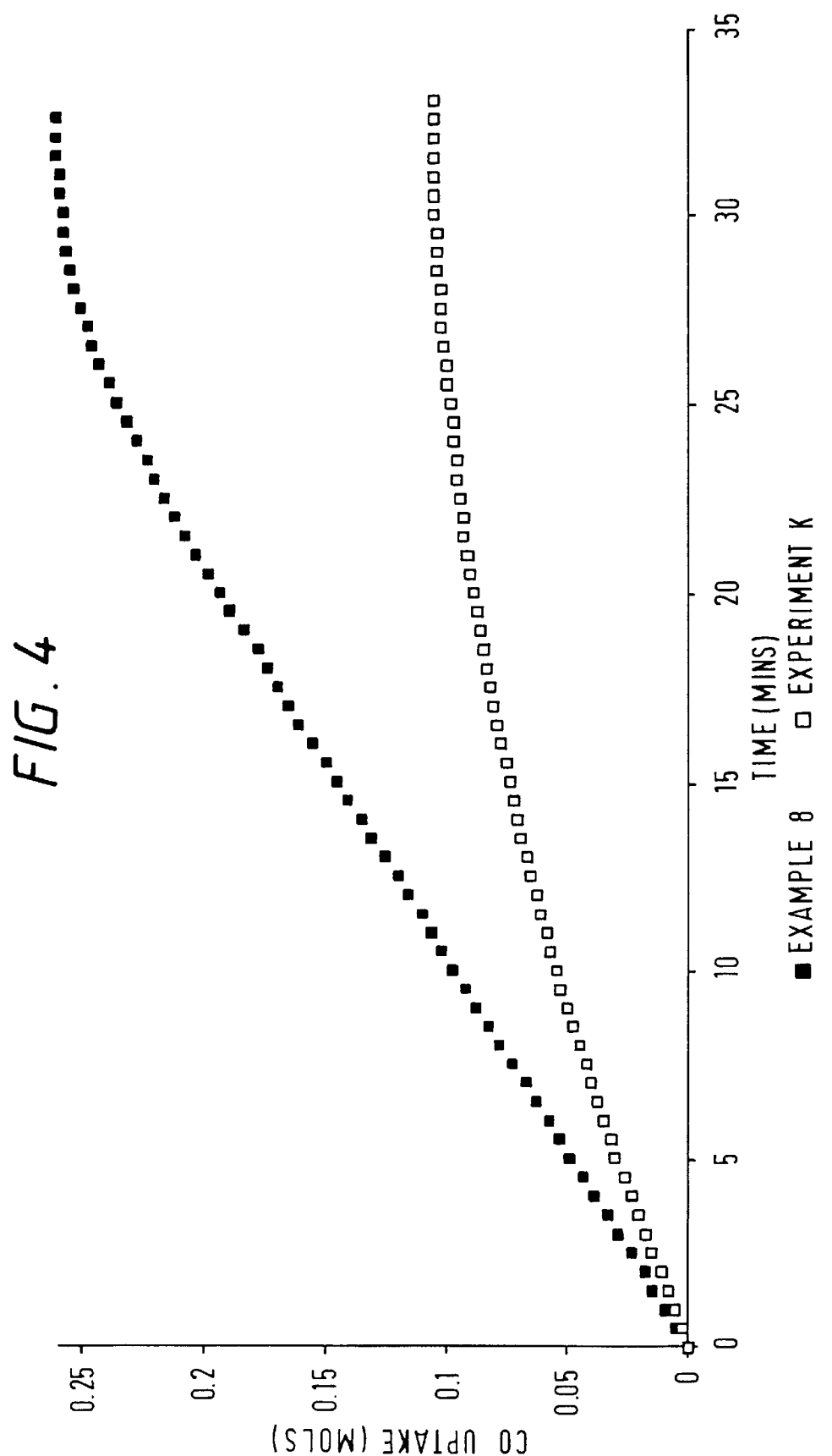
FIG. 4 represents a graph of carbon monoxide uptake against reaction time for Experiment K and Example 8.

The rate of reaction, based upon carbon monoxide uptake rate, after 5 minutes was calculated to be 3.6 mol/l/hr (see FIG. 4). The reaction ceased after only 104 mmol of carbon monoxide had been fed from the ballast vessel. This corresponded to carbonylation of 43% of the methyl acetate reactant. The major (>99%) product detected in the liquid reaction composition at the end of the experiment was acetic acid. The non-condensable gases, measured as before, contained carbon dioxide (4.3%), methane (9.5%) and carbon monoxide (balance). In contrast to Experiment I and Example 7 evidence of extensive catalyst precipitation was observed on opening the autoclave. This catalyst precipitation was due to the low partial pressure of carbon monoxide during the experiment.

This is not an example according to the present invention because no ruthenium or osmium promoter was present in the liquid reaction composition.

EXAMPLE 8

Experiment K was repeated except that $RuCl_3.3H_2O$ (3.93 mmol), methyl acetate (244 mmol), water (906 mmol), methyl iodide (101 mmol), and acetic acid (703 mmol) were charged to the autoclave. The reaction was performed at a constant pressure of 27.6 barg, a carbon monoxide partial pressure of 4.7 bar, and at a temperature of 185° C.

The rate of reaction, based upon carbon monoxide uptake rate, after 5 minutes was calculated to be 6.4 mol/l/hr (see FIG. 4). The reaction continued until all the methyl acetate reactant had been consumed. The major (>99%) product detected in the liquid reaction composition at the end of the experiment was acetic acid. The non-condensable gases, measured as before, contained carbon dioxide (3.7%), methane (2.1%) and carbon monoxide (balance). On opening the autoclave there was no evidence of catalyst precipitation.

This example is according to the present invention and shows the benefit of the presence of ruthenium in the liquid reaction composition on the reaction rate at low partial pressures of carbon monoxide. This example also demonstrates that ruthenium stabilises the rhodium catalyst at low partial pressures of carbon monoxide, such as for example as may be present during separation of product and catalyst during product recovery from the reaction composition which takes place at a partial pressure of carbon monoxide less than that in the carbonylation reaction.

EXAMPLE 9

Example 8 was repeated except that $RuCl_3$ (3.96 mmol), methyl acetate (244 mmol) water (914 mmol), methyl iodide (101 mmol) and acetic acid (703 mmol) were charged to the autoclave at the start before the rhodium catalyst solution was added. The reaction was undertaken at a constant pressure of 27.5 barg, a carbon monoxide partial pressure of 4.6 bar, and at a temperature of 185° C.

The rate of reaction, based upon carbon monoxide uptake rate, after 5 minutes was calculated to be 5.4 mol/l/hr. The reaction was allowed to continue until completion. Subsequent analysis of the liquid reaction composition showed acetic acid (>99%) and acetaldehyde (trace). The non-condensable gases, measured as before, contained carbon dioxide (5.3%), methane (3.1%) and carbon monoxide (balance). There was no evidence of rhodium catalyst precipitation on opening the autoclave.

This example is according to the present invention since it demonstrates that addition of ruthenium to the liquid reaction composition at low partial pressures of carbon monoxide both stabilises the rhodium catalyst and promotes the reaction rate.

Reactions Under Substantially Anhydrous Conditions

Experiment L

In the following Experiments and Examples a Hastelloy (Trade Mark)B2 autoclave similar to that used in the previous experiments and examples was used but having a 300 ml volume. The procedure used was also similar.

The batch autoclave was flushed with carbon monoxide and then charged with acetic acid (30 g, 0.50 moles), acetic anhydride (15 g, 0.147 moles), N-methyl imidazole (10.56 g, 0.129 moles), methyl acetate (45 g, 0.61 moles) and methyl iodide (38.55 g, 0.27 moles). The autoclave was pressurised with carbon monoxide to a pressure of 25.4 barg at ambient temperature. The autoclave contents were heated with stirring (1500 rpm) to 185° C. Once stable at temperature the total pressure in the autoclave was increased to 36 barg by feeding carbon monoxide. Rhodium catalyst [Rh(CO)$_2$Cl]$_2$ (0.2093 g, 0.54 mmoles) dissolved in 10 g of acetic acid was then introduced using an over pressure of carbon monoxide to give a reaction pressure of 39.8 barg. The reaction was carried out at constant pressure (39.8 barg) with carbon monoxide fed on demand from a ballast vessel to maintain the autoclave pressure, until no further gas uptake was observed. The pressure in the ballast vessel was measured every 12 seconds and a third degree polynominal curve was fitted to this data from which the rate of carbonylation (mol/l/hr) was calculated.

The methyl acetate concentration in the reactor was calculated from the carbon monoxide uptake as the reaction progressed. When the methyl acetate concentration was calculated to be 26% by weight the reaction rate was calculated to be 3.5 mol/l/hr.; at 16% by weight calculated methyl acetate concentration the reaction rate was 2.80 mol/l/hr. Methane by product was 0.29 mmol and carbon dioxide by product was 6.93 mmol. Analysis of the final reaction composition showed the concentration of ethylidene diacetate by-product to be 1091 ppm.

The carbon monoxide had a purity of >99.9%, the impurity being mostly nitrogen. Traces of hydrogen below the limit of analytical detection may have been present.

This is not an example according to the present invention because no ruthenium or osmium promoter was present in the liquid reaction composition.

Experiment M

Experiment L was repeated except that $[Ru(CO)_3Cl_2]_2$ (0.2831 g, 0.55 mmoles) and acetic acid (1.0 g, 0.17 mole) were charged to the autoclave at the start prior to flushing the autoclave with carbon monoxide. The autoclave was then charged with acetic acid (39 g), acetic anhydride (15 g), N-methyl imidazole (10.61 g), methyl acetate (45.1 g) and methyl iodide (38.52 g). The autoclave was pressurised with carbon monoxide to a pressure of 25.0 barg at ambient temperature. The autoclave contents were heated with stirring (1500 rpm.) to 185° C. Once stable at temperature the total pressure in the autoclave was increased to 39.8 barg by feeding carbon monoxide. The reaction was carried out at constant pressure (39.8 barg) for a period of 1.5 hours. During this time there was virtually no carbon monoxide gas uptake with a maximum rate of 0.02 mol/l/hr. being observed.

This is not an example according to the present invention because no rhodium catalyst was present in the liquid reaction composition.

EXAMPLE 10

Experiment L was repeated except that $[Ru(CO)_3Cl_2]$ (0.2837 g, 0.55 mmoles) was charged to the autoclave via a charging funnel after flushing the autoclave with carbon monoxide and was washed in with the liquid reaction components, acetic acid (30 g) acetic anhydride (15 g) N-methyl imidazole (10.59 g) methyl acetate (45.1g) and mmethyl iodide (38.71 g). The autoclave was pressurised with carbon monoxide to a pressure of 25.0 barg at ambient temperature and then heated with stirring (1500 rpm) to 185° C. reaction temperature. Once stable at reaction temperature, the total pressure in the autoclave was increased to 35.6 barg by feeding carbon monoxide. The catalyst $[Rh(CO)_2Cl]_2$ (0.2100 g, 0.54 mmoles) dissolved in 10 g of acetic acid was then introduced using, an over pressure of carbon monoxide. The reaction pressure, after injection of the rhodium catalyst solution, was maintained at 39.0 barg. The reaction was performed until no further gas uptake was observed.

When the methyl acetate concentration was calculated to be 26% by weight the reaction rate was calculated to be 4.91 mol/l/hr.; at 16% by weight methyl acetate concentration the reaction rate was 3.40 mol/l/hr. Liquid gas chromatographic analysis of a sample of the liquid reaction composition showed that 940 ppm by weight ethylene diacetate by-product had been formed during the reaction. Analysis of the gases vented from the autoclave, by gas chromatography, showed that 0.58 mmoles of methane and 4.06 mmol carbon dioxide had been formed during the reaction.

This Example is according to the present invention and demonstrates the benefit of the presence of ruthenium in the liquid reaction composition on the carbonylation rate of methyl acetate under substantially anhydrous conditions to produce acetic anhydride.

Experiment N

Experiment L was repeated except that the autoclave was flushed with hydrogen before being charged with acetic acid (32.1 g), acetic anhydride (15 g), N-methyl imidazole (10.57 g), methyl acetate (45 g) and methyl iodide (38.63 g). The reactor was then pressurised with hydrogen to an ambient pressure of 2.0 barg, and then with carbon monoxide to a total pressure of 27 barg and heated to the reaction temperature of 185° C. The catalyst $[Rh(CO)_2Cl]_2$ (0.2103 g) dissolved in 10 g of acetic acid was then introduced using a over pressure of carbon monoxide. The reaction was then progressed as in Experiment L but at a pressure of 39.6 barg.

When the calculated methyl acetate concentration was 26% by weight the reaction rate was calculated to be 7.62 mol/l/l hr.; at 16% by weight methyl acetate concentration the reaction rate was 5.35 mol/l/hr. Analysis of a sample of the liquid reaction composition by liquid gas chromatography showed that 4572 ppm by weight ethylene diacetate by-product had been formed during the reaction. Analysis of the gases vented from the autoclave, by gas chromatography, showed that 11.18 mmoles methane and 2.35 carbon dioxide had been formed during the reaction.

This is not an example according to the present invention because no ruthenium or osmium promoter was present in the liquid reaction composition.

Experiment P

Experiment L was repeated except that the total reaction pressure after injection of the rhodium catalyst solution was maintained at 55 barg.

When the calculated methyl acetate concentration was 26% by weight the reaction rate was calculated to be 4.47 mol/l/hr.; at 16% by weight calculated methyl acetate concentration the reaction rate was 2.93 mmol/l/hr. Analysis of the final reaction composition showed the concentration of ethylidene diacetate by-product to be 1032 ppm.

This is not an example according to the present invention because no ruthenium or osmium promoter was present in the liquid reaction composition.

EXAMPLE 11

Example 10 was repeated except the total reaction pressure was maintained at 55 barg.

When the methyl acetate concentration was 26% by weight the reaction rate was calculated to be 6.2 mol/l/hr.; at 16% by weight methyl acetate concentration the reaction rate was 4.28 mol/l/hr. Analysis of the final reaction composition showed 665 ppm ethylidene diacetate by-product to be present.

This Example is according to the present invention and a comparison with Experiment P demonstrates the benefit of the presence of ruthenium in the liquid reaction composition on carbonylation rates under substantially anhydrous conditions at higher total reaction pressure.

EXAMPLE 12

Example 10 was repeated except that $[Ru(CO)_3Cl_2]_2$ (2.83 g, 5.53 mmoles) and acetic acid (2.09 g) were added to the autoclave prior to flushing with carbon monoxide. The autoclave was then charged with acetic acid (23.6 g), acetic anhydride (15 g), N-methyl imidazole (10.59 g), methyl acetate (45 g) and methyl iodide (41.34 g). The autoclave was pressurised to 25 barg at ambient temperature with stirring (1500 rpm) and then heated to reaction temperature of 185° C. Once stable at reaction temperature, the total pressure in the autoclave was increased to 35.9 barg by feeding carbon monoxide. The reaction pressure, after injection of the rhodium catalyst solution ($[Rh(CO)_2Cl]_2$ (0.2095 g in 10 g acetic acid), was maintained at 39.2 barg.

When the calculated methyl acetate concentration was 26% by weight the reaction rate was calculated to be 6.23 mol/l/hr.; at 16% by weight calculated methyl acetate concentration the reaction rate was 4.12 mol/l/hr. Carbon dioxide by product was 3.49 mmol and methane by-product was 0.58 mmol. Analysis of the final reaction composition showed the concentration of ethylidene diacetate by-product to be 810 ppm.

This Example is according to the present invention and demonstrates the benefit of the presence of ruthenium in the liquid reaction composition on carbonylation rates under substantially anhydrous conditions.

EXAMPLE 13

Example 10 was repeated except that hydrogen was used to flush the autoclave after it had been charged with [Ru(CO)$_3$Cl$_2$]$_2$ (0.2833 g) and acetic acid (1 g, 0.017 mole). The autoclave was then charged with acetic acid (30 g), acetic anhydride (15 g), N-methyl imidazole (10.60 g), methyl acetate (45.2 g) and methyl iodide (38.39 g). Hydrogen was used to pressurise the autoclave to a pressure of 2.0 barg at ambient temperature, and then the autoclave was pressurised with carbon monoxide to a total pressure of 25.1 barg. The autoclave was heated to 185° C. with stirring (1500 ppm). Once stable at temperature the total pressure was increased to 35.3 barg by feeding carbon monoxide. The catalyst was injected and the reaction pressure, after injection of the rhodium catalyst solution, ([Rh(CO)$_2$Cl]$_2$, 0.2105 g in 10 g of acetic acid) was maintained at 39.6 barg.

When the calculated methyl acetate concentration was 26% by weight the reaction rate was calculated to be 8.64 mol/l/hr.; at 16% by weight calculated methyl acetate concentration the reaction rate was 5.76 mol/l/hr. Carbon dioxide by-product was 4.09 mmol and methane by-produce was 11.11 mmol. Analysis of the final reaction composition showed the concentration of ethylidene diacetate by-product to be 7739 ppm.

This Example is according to the present invention and demonstrates the benefit of the presence of ruthenium in the liquid reaction composition on carbonylation rates under substantially anhydrous conditions and in the presence of carbon monoxide and hydrogen in a molar ratio of carbon monoxide: hydrogen of greater than 10:1.

EXAMPLE 14

Example 10 was repeated except that [Ru$_3$(CO)$_{12}$] (0.2306 g,) and acetic acid (1.04 g) were added to the autoclave prior to flushing with carbon monoxide. The autoclave was then charged with acetic acid (29 g), acetic anhydride (15 g), 1 N-methyl imidazole (10.56 g), methyl acetate (45 g) and methyl iodide (38.59 g). The reactor was then pressurised with carbon monoxide to a pressure of 25.3 barg at ambient temperature and heated to 185° C. with stirring (1500 ppm). Once stable at temperature the total pressure in the autoclave was increased to 35.8 barg by feeding carbon monoxide. The reaction pressure, after injection of the rhodium catalyst solution [(Rh(CO)$_2$Cl]$_2$ (0.2098 g) in 10 g of acetic acid), was maintained at 39.6 barg.

When the calculated methyl acetate concentration was 26% by weight the reaction rate was calculated to be 5.47 mol/l/hr.; at 16% by weight calculated methyl acetate concentration the reaction rate was 3.70 mol/l/hr. Carbon dioxide by-product was 3.47 mmol and methane by-product was 1.16 mmol. Analysis of the final reaction composition showed the concentration of ethylidene diacetate by-product to be 1331 ppm.

This Example is according to the present invention and demonstrates the benefit of the presence of ruthenium in the liquid reaction composition on the carbonylation rates under substantially anhydrous conditions.

EXAMPLE 15

Example 10 was repeated except that [Os$_3$(CO)$_{12}$] (0.2973 g, 0.33 mmoles) and acetic acid (1.08 g 0.017 mole) were added to the autoclave prior to flushing with carbon monoxide. The autoclave was then charged with acetic acid (29 g), acetic anhydride (15 g), 1 N-methyl imidazole (10.54 g), methyl acetate (45 g) and methyl iodide (38.59 g). The reactor was then pressurised with carbon monoxide to a pressure of 25.1 barg at ambient temperature and heated to 185° C. with stirring (1500 ppm). Once stable at temperature the total pressure was increased to 35.7 barg by feeding carbon monoxide. The reaction pressure, after injection of the rhodium catalyst solution ([Rh(CO)$_2$Cl]$_2$, 0.2100 g in 10 g of acetic acid), was maintained 39.5 barg.

When the calculated methyl acetate concentration was 26% by weight the reaction rate was calculated to be 6.86 mol/l/hr. ; at 16% by weight calculated methyl acetate concentration the reaction rate was 4.27 mol/l/hr. Carbon dioxide by-product was 3.41 mmol and methane by-product was 0.57 mmol. Analysis of the final reaction composition showed the concentration of ethylidene diacetate by-product to be 1010 ppm.

This Example is according to the present invention and demonstrates the benefit of the presence of osmium in the liquid reaction composition on carbonylation rates under substantially anhydrous conditions.

EXAMPLE 16

Example 10 was repeated except that [Os$_3$(CO)$_{12}$] (1.6267 g) and acetic acid (1.03 g) were added to the autoclave prior to flushing with carbon monoxide. The autoclave was charged with acetic acid (26.2 g), acetic anhydride (15 g), 1 N-methyl imidazole (10.58 g), methyl acetate (45.1 g) and methyl iodide (39.86 g). The autoclave was then pressurised with carbon monoxide to a pressure of 25.9 barg at ambient temperature and heated to 185° C. with stirring (1500 ppm). Once stable at temperature the total pressure was increased to 36.7 barg by feeding carbon monoxide. The reaction pressure, after injection of the rhodium catalyst solution ([Rh(CO)$_2$Cl]$_2$, 0.2108 g in 10 g of acetic acid), was maintained at 40.7 barg.

When the calculated methyl acetate concentration was 26% by weight the reaction rate was calculated to be 7.29 mol/l/hr; at 16% by weight calculated methyl acetate concentration the reaction rate was 4.02 mol/l/hr. Analysis of the liquid reaction composition at the end of the reaction by gel showed 1370 ppm by weight ethylene diacetate by-product to be present. Analysis of the gases vented from the autoclave by gas chromatography showed that 2.93 moles of each of carbon dioxide and methane had formed in the reaction.

This Example is according to the present invention and demonstrates the benefit of the presence of osmium in the liquid reaction composition on carbonylation rates under substantially anhydrous conditions. This Example also shows that the use of osmium promoter enables a reaction rate comparable to that of Experiment N but without the use of hydrogen and therefore with lower amounts of by-product ethylidene diacetate and methane being formed.

EXAMPLE 17

Example 10 was repeated except that RuCl$_3$.3H$_2$O (0.291 g, 1.1 mmoles) and acetic acid (1 g) was added to the autoclave prior to flushing with carbon monoxide and then charging with the following components:

| acetic acid | 29.0 g |
| --- | --- |
| acetic anhydride | 15 g |
| 1-N methyl imidazole | 10.62 g |
| methyl acetate | 45.38 g |
| methyl iodide | 38.42 g |

The autoclave was then pressurised with carbon monoxide to 25.4 barg at ambient temperature and heated to 185° C. with stirring (1500 ppm). Once stable at temperature the total pressure was increased to 36 barg with carbon monoxide before the catalyst [(Rh(CO)$_2$Cl]$_2$, 0.2106 g in 10 g of acetic acid) was injected with an over pressure of carbon monoxide. The reaction was progressed at a constant pressure of 39.9 barg until no further carbon monoxide was taken up.

At a calculated methyl acetate concentration of 26% by weight the reaction rate was calculated to be 2.39 mol/l/hr and at 16% calculated methyl acetate the reaction rate was calculated to be 1.81 mol/l/hr. Carbon dioxide by-product was 2.89 mmol and methane by-product was 0.0 mmol. Analysis of the final reaction composition showed the concentration of ethylidene diacetate by-product to be 606 ppm.

EXAMPLE 18

Example 17 was repeated using similar amounts of reagents:

| RuCl$_3$3H$_2$O (in 1 g acetic acid) | 0.2850 g |
| --- | --- |
| acetic acid (main charge) | 29 g |
| acetic anhydride | 15 g |
| 1 N-methyl imidazole | 10.62 g |
| methyl acetate | 45.1 g |
| methyl iodide | 38.52 g |
| [Rh(CO)$_2$Cl]$_2$ (in 10 g acetic acid) | 0.2104 g |

In this Example however, the autoclave was flushed with hydrogen after it had been charged with the RuCl$_3$3H$_2$O and was initially pressurised with hydrogen to 2.2 barg at ambient temperature and then to a total pressure of 25 barg with carbon monoxide before heating.

The reaction was performed at a total pressure of 39.0 barg until no further uptake of carbon monoxide was observed.

At a calculated methyl acetate concentration of 25% by weight the rate of reaction was 8.51 mol/l/hr and at 16% methyl acetate the rate was 5.83 mol/l/hr. Analysis of the final reaction composition showed the concentration of ethylidene diacetate by-product to be 6407 ppm.

This Example demonstrates the use of hydrogen in combination with RuCl$_3$3H$_2$O.

EXAMPLE 19

Example 18 was repeated Using Os$_3$(CO)$_{12}$ (0.3263, 0.36 mmoles) in place of RuCl$_3$3H$_2$O and the following amounts of reagents and conditions.

| acetic acid with Os$_3$(CO)$_{12}$ | 1.11 g |
| --- | --- |
| acetic acid (main charge) | 29 g |
| acetic anhydride | 15.21 g |
| 1-N-methyl imidazole | 10.65 g |
| methyl acetate | 45 g |
| methyl iodide | 38.56 g |
| [Rh(CO)$_2$Cl]$_2$ (in 10 g acetic acid) | 0.21 g |

| Initial pressurization (hydrogen) | –2.1 barg |
| --- | --- |
| Further pressurization at ambient temperature with carbon monoxide (total pressure) | –25.3 barg |
| Pressure before injection of rhodium catalyst | –35.9 barg |
| Constant reaction pressure | –40.3 barg |

At a calculated methyl acetate concentration of 26% by weight the rate of reaction was 8.30 mol/l/hr and at 16% methyl acetate was 5.54 mol/l/hr. Carbon dioxide by-product was 2.33 mmol and methane by-product was 6.40 mmol. Analysis of the final reaction composition showed the concentration of ethylidene diacetate by-product to be 10992 ppm.

Experiment R

Example 18 was repeated without any ruthenium compound or imidazole co-promoter. The autoclave was flushed with hydrogen prior to charging:

| acetic acid | 59 g |
| --- | --- |
| acetic anhydride | 15 g |
| methyl acetate | 44.98 g |
| methyl iodide | 20.45 g |

The autoclave was pressurised with hydrogen to 2.0 barg at ambient temperature and then to a total pressure of 40 barg with carbon monoxide before heating to 185° C. with stirring (185° C). Once stable at temperature catalyst ([Rh (CO)$_2$Cl]$_2$, 0.2119 g in 10 g of acetic acid) was injected and the reaction progressed at a constant pressure of 54 barg until no further uptake of carbon monoxide was observed.

At a calculated methyl acetate concentration of 26% by weight the rate of reaction was 2.70 mol/l/hr and at 16% calculated methyl acetate was 1.34 mol/l/hr.

EXAMPLE 20

Experiment R was repeated except that [Ru(CO)$_3$Cl$_2$]$_2$ 0.285 g, 0.55 mmoles was charged to the autoclave prior to flushing with hydrogen.

After changing the other components, the initial pressurisation with hydrogen was to 1 barg and with carbon monoxide to a total pressure of 43 barg at ambient temperature.

The catalyst ([Rh(CO)$_2$Cl]$_2$, 0.213 g in 10 g of acetic acid) was introduced and the reaction progressed at a constant pressure of 55 barg until no further carbon monoxide was taken up.

At a calculated methyl acetate concentration of 26% by weight the rate of reaction was 3.37 mol/l/hr and at 16% by weight was 1.98 mol/l/hr. This Example shows the benefits of ruthenium over Experiment R.

Experiment S

This experiment uses an alkali metal iodide, lithium iodide as carbonylation co-promoter.

Experiment L was repeated except that initially LiI (17.14 g, 0.128 mole) was placed in the base of the autoclave under a nitrogen atmosphere and acetic acid (20.01 g, 0.33 mole) was added whilst maintaining the nitrogen cover. The autoclave was then reassembled and flushed with nitrogen and then with carbon monoxide before the following reagents were charged:

| acetic acid | 21.34 g |
| --- | --- |
| acetic anhydride | 15.06 g |

| | |
|---|---|
| methyl acetate | 45.1 g |
| methyl iodide | 20.43 g |

The autoclave was then pressurised with carbon monoxide to 25.9 barg at ambient temperature before being heated to 185° C. with stirrin g (1500 ppm). Once stable temperature had been achieved the total pressure was increased to 36.3 barg by feeding carbon monoxide from the ballast vessel and then the catalyst ([Rh(CO)$_2$Cl]$_2$, 0.2104 g in 10 g of acetic acid) was introduced using an overpressure of carbon monoxide. The reaction progressed at a constant pressure of 40.0 barg until no further carbon monoxide was taken up.

At a calculated methyl acetate concentration of 26% by weight the rate of reaction was 8.81 mol/l/hr and at 16% the rate was 5.66 mol/l/hr. Carbon dioxide by product was 1.72 mmol and methane by-product was 0.57 mmol. Analysis of the liquid reaction composition at the end showed 554 ppm ethylidene diacetate.

This is not an example according to the present invention because no ruthenium or osmium promoter were used.

EXAMPLE 21

Experiment S was repeated except that Ru$_3$(CO)$_{12}$ (0.2303 g, 0.36 mmol) was added initially with the lithium iodide (17.10 g) and acetic acid (21 g). Similar amounts of reagents and conditions were used:

| | |
|---|---|
| acetic acid | 20 g |
| acetic anhydride | 15.04 g |
| methyl acetate | 45.33 g |
| methyl iodide | 20.35 g |
| [(Rh(CO)$_2$Cl]$_2$ in 10 g of acetic acid | 0.2094 g |
| initial pressurization with carbon monoxide | −25.9 barg |
| subsequent pressurization with carbon monoxide | −35.9 barg |
| constant pressure during reaction | −40.0 barg |

At a calculated methyl acetate concentration of 26% by weight the rate of reaction was 10.06 mol/l/hr and at 16% was 5.27 mol/l/hr. Carbon dioxide by-product was 2.30 mmol and methane by-product was 2.30 mmol. Analysis of the liquid reaction composition at the end showed 423 ppm ethylidene diacetate.

This is an Example according to the present invention and shows the benefit of ruthenium with lithium iodide co-promoter for acetic anhydride production.

EXAMPLE 22

Experiment S was repeated except that Os$_3$(CO)$_{12}$ (0.3264 g, 0.36 mmoles) was initially added with the LiI (17.17 g, 0.128 mole) and acetic acid (20 g). Similar amounts of reagents and conditions were used:

| | |
|---|---|
| acetic acid | 20 g |
| acetic anhydride | 15.03 g |
| methyl acetate | 45.13 g |
| methyl iodide | 20.32 g |
| [Rh(CO)$_2$Cl]$_2$ (in 10 g of acetic acid) | 0.2098 g |
| Initial pressurization with carbon monoxide | −26.0 barg |
| Subsequent pressurization | −36.2 barg |
| Constant pressure during reaction | −40.7 barg |

At a calculated methyl acetate concentration of 26% by weight the rate of reaction was 10.70 mol/l/hr and at 16% was 6.10 mol/l/hr. Carbon dioxide by-product was 2.31 mmol and methane by-product was 1.73 mmol. Analysis of the final reaction composition showed the concentration of ethylidene diacetate by-product to be 757 ppm.

This is an example according to the present invention and shows the benefit of osmium with lithium iodide co-promoter for acetic anhydride production.

Experiment T

Experiment S was repeated except that hydrogen was used to flush the autoclave after flushing with nitrogen and the reagents charged were:

| | |
|---|---|
| LiI | 17.18 g |
| with acetic acid | 21 g |
| additional acetic acid | 20.0 g |
| acetic anhydride | 15.02 g |
| methyl acetate | 45 g |
| methyl iodide | 20.29 g |

The autoclave was pressurised with hydrogen to 2.2 barg then with carbon monoxide to a total pressure of 25.9 barg at ambient temperature before heating to 185° C. with stirring (1500 ppm). Once stable temperatures have been achieved the pressure was increased to 35.7 barg by feeding carbon monoxide. Then the catalyst ([Rh(CO)$_2$Cl]$_2$, 0.2104 g) in 10 g of acetic acid) was injected and the reaction progressed at a constant total pressure of 40.6 barg until no further carbon monoxide was taken up.

At a calculated methyl acetate concentration of 26% by weight the rate of reaction was 10.43 mol/l/hr and at 16% was 7.01 mol/l/hr. Carbon dioxide by-product was 2.42 mmol and methane by-product was 14.54 mmol. Analysis of the final reaction composition showed ethyledene diacetate by-product present at 4601 ppm.

EXAMPLE 23

Experiment T was repeated using the following amounts of reagents and conditions:

Initial Charge

| | |
|---|---|
| [Ru(CO)$_3$Cl$_2$]$_2$ | 0.2823 g (0.55 mmol) |
| LiI | 17.25 g |
| acetic acid (initial charge) | 20 g |
| main charge | |
| acetic acid | 20 g |
| acetic anhydride | 15.03 g |
| methyl acetate | 45.45 g |
| methyl iodide | 20.19 g |
| catalyst | |
| [(Rh(CO)$_2$Cl]$_2$ in 10 g of acetic acid) | 0.2107 g |
| pressures | |
| initial pressurization with hydrogen | 2.2 barg |
| subsequent pressurization with carbon monoxide to total pressure | 25.0 barg |
| pressure increased at 185° C. to | 35.0 barg |
| constant reaction pressure | 39.7 barg |

At a calculated methyl acetate concentration of 26% by weight the rate of reaction was 11.67 mol/l/hr and at 16% was 7.87 mol/l/hr. Carbon dioxide by-product was 1.72 mmol and methane by-product was 13.79 mmol. Analysis of the final reaction composition showed the concentration of ethylidene diacetate by-product to be 5644 ppm.

This is an example according to the present invention and shows the benefits of using ruthenium with lithium iodide copromoter and in the presence of carbon monoxide and hydrogen at a ratio of carbon monoxide: hydrogen of greater than 10:1 to produce acetic anhydride.

Experiment U

Repeats of Experiment S consistently resulted in carbonylation rates significantly lower than those reported above. The higher rate achieved in Experiment S may be due to osmium contamination from the prior experiment. In attempting to repeat the experiment problems were experienced with aerial oxidation of the LiI charged to the autoclave prior to reaction. Therefore the following alternative procedure was used:

Experiment L was repeated except that lithium acetate dihydrate (13.10 g, 0.128 mole) was placed in the bottom of the autoclave under a nitrogen atmosphere and acetic acid (1.81 g, 0.03 mole) was added while maintaining the nitrogen cover. The actoclave was then assembled, placed in position and flushed with nitrogen. The autoclave was then flushed with carbon monoxide and charged with acetic acid (9.55 g, 0.16 mole), acetic anhydride (41.33 g, 0.40 moles), methyl acetate (35.66 g, 0.48 moles) and methyl iodide (39.04 g, 0.275 moles). The autoclave was then pressurised with carbon monoxide to an ambient pressure of 25.4 barg. The reactor contents were stirred (1500 r.p.m.) and heated to 185° C. Once stable at temperature the total pressure was increased to 36.2 barg by feeding carbon monoxide from the ballast vessel. The catalyst [Rh(CO)$_2$Cl]$_2$(0.2109 g, 0.54 mmoles) dissolved in 10 g of acetic acid was introduced using an overpressure of carbon monoxide to give a reaction pressure of 41.1 barg. The reaction was carried out at constant pressure (41.1 barg) until no further gas uptake was observed.

The methyl acetate concentration in the reactor was calculated from the carbon monoxide uptake as the reaction progressed. When the methyl acetate concentration was 26% by weight the reaction rate was calculated to be 3.77 mol/l/hr.; at 16% w/w methyl acetate the reaction rate was 2.53 mol/tr/hr.

Carbon dioxide by-product was 2.34 mmol and methane by-product was 0.59 mmol. Analysis of the liquid reaction composition at the end showed 346 ppm ethylidene diacetate.

Experiment V

Experiment L was repeated except that the autoclave was flushed three times with carbon monoxide and then once with a mixture of ca. 0.25% hydrogen in carbon monoxide. The carbon monoxide/hydrogen gas mixture was used to pressurise the reactor, to inject the catalyst and as feed from the ballast vessel. The following components were charged to the autoclave:

| Acetic acid | 29.82 g |
| Acetic anhydride | 15.01 g |
| Methyl acetate | 45.10 g |
| Methyl iodide | 38.53 g |
| 1-N-methyl imidazole | 10.56 g |
| [Rh(CO$_2$)Cl]$_2$ in 10 g acetic acid | 0.2110 g |

The autoclave was then pressurised with a mixture of hydrogen and carbon monoxide (0.248% H$_2$) to 25.1 barg. Once stable at temperature the total pressure was increased to 35.1 barg. The reaction was progressed at a constant pressure of 40.0 barg.

At a calculated methyl acetate concentration of 26% by weight the reaction rate was calculated to be 7.65 mol/l/hr, and at 16% by weight calculated methyl acetate concentration the reaction rate was calculated to be 5.43 mol/l/hr. Carbon dioxide by-product was 4.47 mmol and methane by-product was 1.12 mmol. Analysis of the final reaction composition showed the concentration of ethylidene diacetate by-product to be 2016 ppm.

EXAMPLE 24

Experiment V was repeated except that 0.2308 g of Ru$_3$(CO)$_{12}$ and 1 g of acetic acid were added to the autoclave as an initial charge before flushing. The following components were subsequently charged to the autoclave:

| Acetic acid | 29.13 g |
| Acetic anhydride | 15.02 g |
| Methyl acetate | 45.00 g |
| Methyl iodide | 38.69 g |
| 1-N-methyl imidazole | 10.51 g |
| [Rh(CO$_2$)Cl]$_2$ in 10 g acetic acid | 0.2096 g |

At a calculated methyl acetate concentration of 26% by weight the rate of reaction was calculated to be 8.45 mol/l/l hr, and at 16% by weight calculated methyl acetate the reaction rate was calculated to be 5.88 mol/l/hr. Carbon dioxide by-product was 1.75 mmol and methane by-product was 1.17 mmol. Analysis of the final reaction composition showed the concentration of ethylidene diacetate by-product to be 1529 ppm.

This is an example according to the present invention and shows the benefit of ruthenium in the liquid reaction composition on carbonylation rate and concentration of by-products in the presence of 1 N-methyl imidazole promoter and under substantially anhydrous conditions.

Experiment W

Experiment V was repeated except that a mixture of ca. 0.1% hydrogen in carbon monoxide was used.

At a calculated methyl acetate concentration of 26% by weight the rate of reaction was calculated to be 6.25 mol/l/hr, and at 16% by weight calculated methyl acetate concentration the reaction rate was calculated to be 4.34 mol/l/hr. Carbon dioxide by-product was 3.47 mmol and methane by-product was 0.58 mmol. Analysis of the final reaction composition showed the concentration of ethylidene diacetate by-product to be 1102 ppm.

EXAMPLE 25

Experiment W was repeated except that 0.2308 g of Ru$_3$(CO)$_{12}$ and 1.10 g of acetic acid were added to the autoclave as an initial charge before flushing. The following components were subsequently charged to the autoclave:

| Acetic acid | 28.95 g |
| Acetic anhydride | 15.01 g |
| Methyl acetate | 45.23 g |
| Methyl iodide | 38.53 g |
| 1-N-methyl imidazole | 10.45 g |
| [Rh(CO$_2$)Cl]$_2$ in 10 g acetic acid | 0.2103 g |

At a calculated methyl acetate concentration of 26% by weight the rate of reaction was calculated to be 7.46 mol/l/hr, and at 16% by weight calculated methyl acetate concentration the reaction rate was calculated to be 5.13 mol/l/hr. Carbon dioxide by-product was 3.88 mmol and methane by-product was 1.66 mmol. Analysis of the final reaction composition showed the concentration of ethylidene diacetate by-product to be 1420 ppm.

This is an example according to the present invention and shows the benefit of ruthenium in the liquid reaction composition on carbonylation rate and concentration of by-products in the presence of 1 N-methyl imidazole promoter under substantially anhydrous conditions.

Experiment X

Experiment V was repeated except that a mixture of ca. 0.05% hydrogen in carbon monoxide was used. The following components were charged to the autoclave:

| | |
|---|---|
| Acetic acid | 29.72 g |
| Acetic anhydride | 15.00 g |
| Methyl acetate | 45.10 g |
| Methyl iodide | 38.72 g |
| 1-N-methyl imidazole | 10.56 g |
| [Rh(CO$_2$)Cl]$_2$ in 10 g acetic acid | 0.2098 g |

The reaction pressure was 39.4 barg.

At a calculated methyl acetate concentration of 26% by weight the rate of reaction was calculated to be 5.67 mol/l/hr, and at 16% by weight calculated methyl acetate concentration the reaction rate was calculated to be 3.99 mol/l/hr. Carbon dioxide by-product was 4.00 mmol and methane by-product was 0.29 mmol. Analysis of the final reaction composition showed the concentration of ethylidene diacetate by-product to be 914 ppm.

EXAMPLE 26

Experiment X was repeated except that 0.2304 g of Ru$_3$(CO)$_{12}$ and 1.04 g of acetic acid were added to the autoclave as an initial charge before flushing and the amount of acetic acid subsequently charged to the autoclave was 29 g.

At a calculated methyl acetate concentration of 26% by weight the rate of reaction was calculated to be 7.45 mol/l/hr, and at 16% by weight calculated methyl acetate concentration the reaction rate was calculated to be 5.12 mol/l/hr. Carbon dioxide by-product was 3.46 mmol and methane by-product was 0.29 mmol. Analysis of the final reaction composition showed the concentration of ethylidene diacetate by-product to be 1181 ppm.

This is an example according to the present invention and shows the benefit of ruthenium in the liquid reaction composition on carbonylation rate and concentration of by-products in the presence of 1 N-methyl imidazole promoter and under substantially anhydrous conditions.

Experiment Y

Experiment T was repeated using the following amounts of reagents and conditions:

| initial charge | |
|---|---|
| LiI | 17.21 g |
| acetic acid | 20.01 g |
| main charge | |
| acetic acid | 20.06 g |
| acetic anhydride | 15.05 g |
| methyl acetate | 45.13 g |
| Methyl iodide | 20.35 g |
| catalyst | |
| [Rh(CO$_2$Cl]$_2$ in 10 g acetic acid | 0.2101 g |
| pressures | |
| initial pressurization with hydrogen | 0.09 bara |
| subsequent pressurization with carbon monoxide | 25.1 barg |
| pressure increased at 185° C. to | 35.8 barg |
| constant reaction pressure | 40.2 barg |

At a calculated methyl acetate concentration of 26% by weight the rate of reaction was calculated to be 9.52 mol/l/hr, and at 16% by weight calculated methyl acetate concentration the reaction rate was calculated to be 6.39 mol/l/hr. Carbon dioxide by-product was 1.16 mmol and methane by-product was 11.06 mmol. Analysis of the final reaction composition showed the concentration of ethylidene diacetate by-product to be 475 ppm.

EXAMPLE 27

Experiment Y was repeated except that [Ru(CO)$_3$Cl$_2$]$_2$ (0.2841 g) was included in the initial charge. The autoclave was initially pressurised with hydrogen to 0.09 bara, was subsequently pressurised with carbon monoxide to 24.2 barg, the pressure was increased at 185° C. to 35.3 barg and the reaction was carried out at a constant pressure of 39.6 barg At a calculated methyl acetate concentration of 26% by weight the rate of reaction was 10.79 mol/l/hr, and at a calculated methyl acetate concentration of 16% by weight the reaction rate was calculated to be 7.09 mol/l/hr. Carbon dioxide by-product was 1.13 mmol and methane by-product was 1.70 mmol. Analysis of the final reaction composition showed the concentration of ethylidene diacetate by-product to be 700 ppm.

This Example is according to the present invention and demonstrates the benefit of ruthenium in the liquid reaction composition on carbonylation rate and concentration of by-products in the presence of LiI promoter under substantially anhydrous conditions.

Experiment Z

Experiment U was repeated except that the autoclave was flushed three times with carbon monoxide and then once with a mixture of ca. 0.1% hydrogen in carbon monoxide. This mixture was then used instead of pure carbon monoxide to pressurise the autoclave, introduce the catalyst, and as feed from the ballast vessel. Nitrogen cover was not rigorously used when charging the initial charge. Reagents and conditions were as follows:

| initial charge | |
|---|---|
| lithium acetate dihydrate | 13.23 g |
| acetic acid | 11.02 g |
| main charge | |
| acetic anhydride | 41.29 g |
| methyl acetate | 35.79 g |
| methyl iodide | 38.96 g |
| catalyst | |
| [Rh(CO$_2$Cl]$_2$ in 10 g acetic acid | 0.2096 g |
| pressures | |
| Initial pressurization with 0.11% H$_2$/CO | 25.3 barg |
| Subsequent pressurization with 0.11% H$_2$/CO | 35.1 barg |
| Constant pressure during reaction | 40.1 barg |

At a calculated methyl acetate concentration of 26% by weight the rate of reaction was calculated to be 5.93 mol/l/hr, and at 16% by weight calculated methyl acetate concentration the reaction rate was calculated to be 4.97 mol/l/hr. Carbon dioxide by-product was 2.88 mmol and methane by-product was 1.15 mmol. Analysis of the final reaction composition showed the concentration of ethylidene diacetate by-product to be 495 ppm.

EXAMPLE 28

Experiment Z was repeated except that 0.2306 g of Ru$_3$(CO)$_{12}$ was added to the initial charge. and the reaction pressure was 39.5 barg.

At a calculated methyl acetate concentration of 26% by weight the rate of reaction was calculated to be 9.36 mol/l/hr, and at 16% by weight calculated methyl acetate concentration the reaction rate was calculated to be 6.51 mol/l/hr. Carbon dioxide by-product was 2.28 mmol and methane by-product was 1.71 mmol. Analysis of the final reaction composition showed the concentration of ethylidene diacetate by-product to be 740 ppm.

This Example is according to the present invention and demonstrates the benefit of ruthenium in the liquid reaction composition on carbonylation rate and concentration of by-products under substantially anhydrous conditions when lithium acetate is added to the reaction composition.

Experiment AA

Experiment Z was repeated except that a mixture of ca. 0.25% hydrogen in carbon monoxide was used.

At a calculated methyl acetate concentration of 26% by weight the rate of reaction was calculated to be 7.84 mol/l/hr and at 16% calculated methyl acetate concentration was calculated to be 6.14 mol/l/hr. Carbon dioxide by-product was 1.15 mmol and methane by-product was 1.15 mmol. Analysis of the final reaction composition showed the concentration of ethylidene diacetate by-product to be 681 ppm.

EXAMPLE 29

Experiment AA was repeated except that 0.2308 g of $Ru_3(CO)_{12}$ was added to the initial charge. Similar reagent quantities and conditions were used.

At a calculated methyl acetate concentration of 26% by weight the rate of reaction was calculated to be 9.95 mol/l/hr, and at 16% calculated methyl acetate concentration the reaction rate was calculated to be 6.88 mol/l/hr. Carbon dioxide by-product was 2.24 mmol and methane by-product was 2.24 mmol. Analysis of the final reaction composition showed the concentration of ethylidene diacetate by-product to be 1227 ppm.

EXAMPLE 30

Experiment U was repeated with the following components being charged to the autoclave:

| initial charge | |
|---|---|
| $Ru_3(CO)_{12}$ | 0.2313 g |
| Lithium acetate dihydrate | 13.14 g |
| Acetic acid | 11.02 g |
| main charge | |
| Acetic anhydride | 41.41 g |
| Methyl acetate | 35.72 g |
| Methyl iodide | 38.98 g |
| catalyst | |
| $[Rh(CO)_2Cl]_2$ in 10 g acetic acid | 0.2095 g |
| pressures | |
| Initial pressurization with carbon monoxide | 25.3 barg |
| subsequent pressurization to | 36.0 barg |
| Constant pressure during reaction | 39.9 barg |

At a calculated methyl acetate concentration of 25% by weight the rate of the reaction was calculated to be 9.72 mol/l/hr, and at 16% by weight calculated methyl acetate concentration the reaction rate was calculated to be 5.13 mol/l/hr. Carbon dioxide by-product was 2.26 mmol, and methane by-product was 2.26 mmol. Analysis of the final reaction composition showed the concentration of ethylidene diacetate by-product to be 459 ppm.

EXAMPLE 31

Experiment U was repeated with the following components being charged to the autoclave:

| initial charge | |
|---|---|
| $Ru_3(CO)_{12}$ | 2.30 g |
| Lithium acetate dihydrate | 13.13 g |
| Acetic acid | 6.10 g |
| main charge | |
| Acetic anhydride | 41.54 g |
| Methyl acetate | 35.71 g |
| Methyl iodide | 41.75 g |
| catalyst | |
| $[Rh(CO)_2Cl]_2$ in 10 g acetic acid | 0.2105 g |
| pressures | |
| Initial pressurization with carbon monoxide | 25.0 barg |
| subsequent pressurization to | 36.0 barg |
| Constant pressure during reaction | 39.2 barg |

At a calculated methyl acetate concentration of 25% by weight the rate of the reaction was 11.03 mol/l/hr, and at 16% by weight calculated methyl acetate concentration the reaction rate was 6.51 mol/l/hr. Carbon dioxide by-product was 2.21 mmol, and methane by-product was 10.50 mmol. Analysis of the final reaction composition showed the concentration of ethylidene diacetate by-product to be 1750 ppm.

EXAMPLE 32

Example 30 was repeated except that hydrogen was used to purge the autoclave and the pressures were as follows:

| Initial pressurization with hydrogen | 2.2 barg |
|---|---|
| Further pressurization with carbon monoxide to | 25.1 barg |
| Subsequent pressurization before catalyst injection | 35.6 barg |
| Constant pressure during reaction | 39.7 barg |

At a calculated methyl acetate concentration of 25% by weight the rate of the reaction was 12.62 mol/l/hr, and at 16% by weight calculated methyl acetate concentration was calculated to be 8.70 mol/l/hr. Carbon dioxide by-product was 2.84 mmol, and methane by-product was 21.59 mmol. Analysis of the final reaction composition showed the concentration of ethylidene diacetate by-product to be 7542 ppm.

Examples 31 and 32 show that ruthenium at a molar ratio to rhodium of 10:1 with a lithium iodide co-promoter increases reaction rate compared to that at a molar ratio of 1:1 but that there is an increase in by-product make. The corresponding increase in by-product make with 10:1 Ru:Rh with N,N dimethyl imidazolium iodide was less than with lithium iodide co-promoter.

Data from the preceding experiments and examples for carbonylation reactions under anhydrous conditions are plotted in graph form in FIGS. 5 and 6 which show respectively the effect of ruthenium on the rate of a rhodium catalysed anhydrous carbonylation process with lithium iodide and N N dimethyl imidazolium iodide co-promoters.

The data shown at 9.5% hydrogen was obtained by feeding 2 bar hydrogen to the autoclave and pure carbon monoxide from the ballast vessel, the hydrogen concentration being an estimate. In other cases a hydrogen/carbon monoxide feed gas was used.

FIGS. 5 and 6 show that ruthenium promotes the reaction rate over that of rhodium alone for both lithium iodide and N N dimethyl imidazolium iodide co-promoted anhydrous carbonylation at various hydrogen concentrations. The results also show that with the ruthenium promoter the reaction rate is maintained as hydrogen concentration is decreased so that the process may be operated with a lower hydrogen partial pressure and hence lower by-product formation. This effect is more pronounced for lithium iodide co-promoter than for N N dimethyl imidozalium iodide co-promoter.

Stability Tests

A 150 ml Hastelloy B2 (Trade Mark) autoclave equipped with a Magnedrive (Trade Mark) stirrer and liquid injection facility was used to prepare solutions for the following stability tests.

For each stability test the autoclave was charged with rhodium catalyst, ruthenium or osmium promoter and the liquid components of the liquid reaction composition excluding methyl acetate.

The autoclave was flushed twice with nitrogen and once with carbon monoxide, and was then heated with stirring (1000 rpm) to 185° C. under a carbon monoxide pressure of 3 barg. After allowing the system to reach 185° C., carbon monoxide was introduced into the autoclave and the pressure was subsequently maintained at 27 barg with carbon monoxide for 30 minutes.

The autoclave was then isolated from the gas supply and subsequently cooled to room temperature. The gases were cautiously vented from the autoclave and the liquid reaction composition was discharged. Methyl acetate was then added to the liquid reaction composition.

The liquid reaction composition was then analysed by gas chromatography and methyl iodide was added to the composition to restore the methyl iodide concentration to 2% w/w. A small volume (25 ml) of the composition was then placed in a glass pressure vessel, and heated to 130° C., under a nitrogen pressure of 2 barg. A sample of this heated solution was subsequently removed from the glass pressure vessel, centrifuged and analysed for rhodium by atomic absorption spectroscopy. The remaining solution was maintained at 130° C. for 23 hours, after which a further sample was taken and analysed for rhodium.

Experiment BB

A baseline experiment was performed with the autoclave charged with water (611 mmol), methyl iodide (14 mmol), acetic acid (1396 mmol) and rhodium carbonyl chloride dimer (0.296 mmol). After discharging the autoclave methyl acetate (11 mmol) and methyl iodide (10 mmol) were added to the liquid reaction composition.

The initial concentration of rhodium in solution was found to be 625 ppm. After being heated at 130° C. for 23 hours the rhodium concentration in solution had decreased to 58 ppm. This represented a precipitation of 90.7% of the rhodium from the composition.

This is not an example according to the present invention because no ruthenium or osmium promoter was present in the liquid reaction composition.

EXAMPLE 33

Experiment BB was repeated except that the autoclave was also charged with 20 molar equivalents of ruthenium trichloride hydrate per rhodium carbonyl chloride dimer.

The initial concentration of rhodium in the liquid composition was found to be 608 ppm, whereas after 23 hours the concentration had decreased to 270 ppm. This represented a precipitation of 55.6% of the rhodium from the solution.

This is an example according to the present invention as it demonstrates that addition of ruthenium enhances rhodium stability at low carbon monoxide partial pressures, for example, during the product recovery stage of the process.

We claim:

1. A process for the production of a carboxylic acid having (n+1) carbon atoms by the carbonylation of an alkyl alcohol having n carbon atoms or a reactive derivative thereof (wherein n=1 to 4) which process comprises contacting said alkyl alcohol or reactive derivative thereof with carbon monoxide in a liquid reaction medium at a pressure in the range from 1 to 100 barg and in the presence of (a) a catalyst composition consisting essentially of (i) a rhodium catalyst, (ii) a promoter comprising at least one of ruthenium and osmium and (iii) an alkyl halide and (b) from 0.1% up through 7.0% by weight of water based on the total weight of the liquid reaction medium.

2. A process as claimed in claim 1 in which the liquid reaction composition further comprises the ester of the alcohol and/or reactive derivative thereof and the carboxylic acid product at a concentration in the range 0.1 to 50% by weight.

3. A process as claimed in claim 2 in which the ester concentration is greater than 1.2% and 50% or less by weight.

4. A process as claimed in claim 1 in which carbon monoxide is present in the reactor at a partial pressure of from 1 to less than 15 bar.

5. A process as claimed in claim 4 in which carbon monoxide is present in the reactor at a partial pressure of from 1 to less than 5 bar.

6. A process as claimed in claim 1 in which said carbonylation product is separated from said rhodium catalyst at a partial pressure of carbon monoxide less than that in the reactor.

7. A process as claimed in claim 1 in which additionally hydrogen is present in the reactor at a ratio of carbon monoxide:hydrogen greater than 10:1 molar.

8. A process as claimed in claim 1 in which hydrogen is present in the reactor at a partial pressure up to 0.5 bar.

9. A process as defined in claim 1 in which the promoter (ii) is osmium.

10. A process as defined in claim 1 in which the promoter (ii) is ruthenium.

* * * * *

UNITED STATES PATENT AND TRADEMARK OFFICE
CERTIFICATE OF CORRECTION

PATENT NO.   :   5,939,585

DATED        :   August 17, 1999

INVENTOR(S)  :   EVERT JAN DITZEL ET AL.

It is certified that error appears in the above-identified patent and that said Letters Patent is hereby corrected as shown below:

Column 3, line 32, change "tetraclilorobis..." to --tetrachlorobis...--

Column 3, line 38, change "pentachloro-p..." to --pentachloro-μ...--

Column 13, line 32, change "mmethyl" to --methyl--

Column 16, line 46, change "gel" to --glc--

Signed and Sealed this

Eighth Day of February, 2000

Attest:

Q. TODD DICKINSON

*Attesting Officer*  *Commissioner of Patents and Trademarks*